US011274114B2

(12) United States Patent
Kalyanaramn et al.

(10) Patent No.: US 11,274,114 B2
(45) Date of Patent: Mar. 15, 2022

(54) MODIFIED MITO-METFORMIN COMPOUNDS AND METHODS OF SYNTHESIS AND USE THEREOF

(71) Applicants: THE MEDICAL COLLEGE OF WISCONSIN, INC., Milwaukee, WI (US); UNIVERSITE D'AIX-MARSEILLE 1, Marseilles (FR); Iowa State University Research Foundation, Inc., Ames, IA (US)

(72) Inventors: Balaraman Kalyanaramn, Milwaukee, WI (US); Micael J. Hardy, Nimes (FR); Marcos Lopez, Floridablanca (CO); Olivier Ouari, Seynod (FR); Jacek Michal Zielonka, Wauwatosa, WI (US)

(73) Assignees: The Medical College of Wisconsin, Inc., Milwaukee, WI (US); AIX-Marseille Universite, Marseilles (FR); Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/503,827

(22) PCT Filed: Aug. 13, 2015

(86) PCT No.: PCT/US2015/045075
§ 371 (c)(1),
(2) Date: Feb. 14, 2017

(87) PCT Pub. No.: WO2016/025725
PCT Pub. Date: Feb. 18, 2016

(65) Prior Publication Data
US 2017/0275313 A1 Sep. 28, 2017

Related U.S. Application Data

(60) Provisional application No. 62/037,143, filed on Aug. 14, 2014.

(51) Int. Cl.
C07F 9/54 (2006.01)
C07D 213/20 (2006.01)
A61K 31/662 (2006.01)
A61K 31/155 (2006.01)
A61K 31/4425 (2006.01)

(52) U.S. Cl.
CPC .......... C07F 9/5456 (2013.01); A61K 31/155 (2013.01); A61K 31/4425 (2013.01); A61K 31/662 (2013.01); C07D 213/20 (2013.01); C07F 9/5442 (2013.01)

(58) Field of Classification Search
CPC .... C07F 9/5456; C07F 9/5442; A61K 31/155; A61K 31/4425; A61K 31/662; C07D 213/20
See application file for complete search history.

(56) References Cited

U.S. PATENT DOCUMENTS

| | | | |
|---|---|---|---|
| 9,956,233 B2 * | 5/2018 | Kanthasamy | ........ A61K 31/662 |
| 2009/0214437 A1 | 8/2009 | Kalyanaraman | |
| 2011/0257432 A1 | 10/2011 | DiMauro | |
| 2012/0220664 A1 | 8/2012 | Struhl | |

FOREIGN PATENT DOCUMENTS

| | | | | |
|---|---|---|---|---|
| WO | WO-9105003 A1 * | 4/1991 | ............. | A01N 57/34 |
| WO | 2008/109740 | 9/2008 | | |
| WO | 2010/100337 | 9/2010 | | |
| WO | 2010100337 | 9/2010 | | |
| WO | 2013/103384 | 7/2013 | | |
| WO | 2013103384 | 7/2013 | | |
| WO | 2014/009222 | 1/2014 | | |

OTHER PUBLICATIONS

Legros, A. WO 91/05003 A1 English machine translation (1991) (Year: 1991).*
Salminen et al. J. Neurochem. 2011, 118, 460-474. (Year: 2011).*
U.S. Appl. No. 16/472,640, filed Jun. 2019, Kalyanaraman, B.*
International Search Report and Written Opinion dated Nov. 19, 2015 for International Application No. PCT/US2015/045075.
Zhang X, et al. Induction of mitochondrial dysfunction as a strategy for targeting tumour cells in metabolically compromised microenvironments. Nat Commun 2014; 5:3295.
Zimmerman NP, et al. Cyclic AMP regulates the migration and invasion potential of human pancreatic cancer cells. Mol Carcinog 2015; 54:203-15.
Intrernational Search Report and Written Opinion, PCT/US15/45075, dated Nov. 19, 2015.
Anantharam V. et al. Pharmacological inhibition of neuronal NADPH oxidase protects against 1-methyl-4-phenylpyridinium (MPP+)-induced oxidative stress and apoptosis in mesencephalic dopaminergic neuronal cells. Neurotoxico/ogy 28:988-97, 2007.
Beckham TH, et al. LCL124, a cationic analog of ceramide, selectively induces pancreatic cancer cell death by accumulating in mitochondria. J Pharmacol Exp Ther 2013; 344:167-78.
Birsoy K, et al. Untuning the tumor metabolic machine: Targeting cancer metabolism: a bedside lesson. Nat Med 2012; 18:1022-3.
Bridges HR, et al. Effects of metformin and other biguanides on oxidative phosphorylation in mitochondria. Biochem J 2014; 462:475-87.
Chacko B et al. Prevention of diabetic nephropathy in Ins2+/-AkitaJ mice by the mitochondria-targeted therapy Mito-Q. Biochem J 432:9-19, 2010.
Chandran K et al. Doxorubicin inactivates myocardial cytochrome c oxidase in rats: Cardioprotection by Mito-Q. Biophys J 96:1388-98, 2009.
Cheng G, et al. Mitochondria targeted drugs synergize with 2-deoxyglucose to trigger breast cancer cell death. Cancer Res 2012; 72:2634-44.

(Continued)

Primary Examiner — Amanda L. Aguirre
(74) Attorney, Agent, or Firm — Quarles & Brady LLP

(57) ABSTRACT

The present invention provides mito-metformin compounds, pharmaceutical compositions thereof, and methods of using the mito-metformin compounds in the treatment of cancer.

11 Claims, 23 Drawing Sheets

(56) References Cited

OTHER PUBLICATIONS

Cheng G, et al. Mitochondria-targeted vitamin E analogs inhibit breast cancer cell energy metabolism and promote cell death. BMC Cancer 2013; 13:285.

Cheng G, et al. Profiling and targeting of cellular bioenergetics: inhibition of pancreatic cancer cell proliferation. Br J Cancer 2014; 111:85-93.

Cheng G, et al. Antiproliferative effects of mitochondria-targeted cationic antioxidants and analogs: role of mitochondrial bioenergetics and energy-sensing mechanism. Cancer Lett May 21, 2015; 365(1):96-106.

Cunniff B, et al. Mitochondrial-targeted nitroxides disrupt mitochondrial architecture and inhibit expression of peroxiredoxin 3 and FOXM1 in malignant mesothelioma cells. J Cell Physiol 2013; 228:835-45.

Dowling RJ, et al. Understanding the benefit of metformin use in cancer treatment. BMC Med 2011; 9:33.

Dowling RJ, et al. Changes in insulin receptor signaling underlie neoadjuvant metformin administration in breast cancer: a prospective window of opportunity neoadjuvant study. Breast Cancer Res 2015; 17:32.

Divakaruni AS, et al. Thiazolidinediones are acute, specific inhibitors of the mitochondrial pyruvate carrier. Proc Natl Acad Sci U S A 2013; 110(14):5422-7.

Dranka BP et al., Diapocynin prevents early Parkinson's disease symptoms in the Leucine-Rich Repeat Kinase 2 (LRRK2R1441G) transgenic mouse. Neurosci Lett 549:57-62, 2013.

Dranka BP et al., A novel mitochondrially-targeted apocynin derivative prevents hyposmia and loss of motor function in the leucine-rich repeat kinase 2 (LRRK2R1441 G) transgenic mouse model of Parkinson's disease. Neurosci Lett 583:159-64, 2014.

Durand RE, et al. Radiosensitization of hypoxic cells of an in vitro tumor model by respiratory inhibitors. Radiat Res 1977; 69:359-66.

Emami RA, et al. Metformin and cancer: from the old medicine cabinet to pharmacological pitfalls and prospects. Trends Pharmacol Sci 2013; 34:126-35.

Fasih A, et al. Radiosensitization of pancreatic cancer cells by metformin through the AMPK pathway. Radiat Res 2014; 182(1):50-9.

Ghosh A et al., Neuroprotection by mitochondria-targeted drug in Parkinson's disease model. Free Radic Biol Med 49:1674-84, 2010.

Ghosh A et al., Anti-inflammatory and neuroprotective effects of an orally active apocynin derivative in pre-clinical models of Parkinson's disease. J Neuroinflammation 9(1 ):241-, 2012.

Hardie DG, et al. AMPK: regulating energy balance at the cellular and whole body levels. Physiology (Bethesda) 2014;29:99-107.

Hwang AB, et al. Feedback regulation via AMPK and HIF-1 mediates ROS-dependent longevity in Caenorhabditis elegans. Proc Natl Acad Sci U S A 2014;111(42):E4458-67.

Inoki K, et al. TSC2 mediates cellular energy response to control cell growth and survival. Cell 2003; 115:577-90.

Isebaert SF, et al. 5-aminoimidazole-4-carboxamide riboside enhances effect of ionizing radiation in PC3 prostate cancer cells. Int J Radiat Oncol Biol Phys 2011; 81:1515-23.

Jin H et al., Mitochondria-targeted antioxidants for treatment of Parkinson's disease: Preclinical and clinical outcomes. Biochim Biophys Acta 184:1282-94, 2014.

Kim MP, et al. Generation of orthotopic and heterotopic human pancreatic cancer xenografts in immunodeficient mice. Nature Protocols 2009; 4:1670-80.

Kwong SC, et al. Phenformin and lactic acidosis: a case report and review. J Emerg Med 1998; 16:881-6.

Liu et al. et al. Discrete mechanisms of mTOR and cell cycle regulation by AMPK agonists independent of AMPK. Proc Natl Acad Sci U S A 2014; 111(4):E435-44.

Madiraju AK, et al. Metformin suppresses gluconeogenesis by inhibiting mitochondrial glycerophosphate dehydrogenase. Nature 2014; 510:542-6.

Modica-Napolitano JS, et al. Delocalized lipophilic cations selectively target the mitochondria of carcinoma cells. Adv Drug Deliv Rev 2001; 49:63-70.

Newick K, et al. Peroxiredoxin 3 is a redox-dependent target of thiostrepton in malignant mesothelioma cells. PLoS One 2012; 7:e39404.

Pollak MN. Investigating metformin for cancer prevention and treatment: the end of the beginning. Cancer Discov 2012;2:778-90.

Roy I, et al. CXCL12 chemokine expression suppresses human pancreatic cancer growth and metastasis. PLoS One 2014;9(3):e90400.

Roy I, et al. Pancreatic cancer cell migration and metastasis is regulated by chemokine-biased agonism and bioenergetic signaling. Cancer Res 2015; 75(17):3529-3542.

Sadeghi N, et al. Metformin use is associated with better survival of diabetic patients with pancreatic cancer. Clin Cancer Res 2012; 18:2905-12.

Salabei JK, et al. Comprehensive measurement of respiratory activity in permeabilized cells using extracellular flux analysis. Nat Protoc 2014; 9:421-38.

Sanli T, et al. Ionizing radiation activates AMP-activated kinase (AMPK): a target for radiosensitization of human cancer cells. Int J Radiat Oncol Biol Phys 2010; 78(1):221-9.

Sanli T, et al. Ionizing radiation regulates the expression of AMP-activated protein kinase (AMPK) in epithelial cancer cells: modulation of cellular signals regulating cell cycle and survival. Radiother Oncol 2012; 102:459-65.

Secomb TW, et al. Analysis of the effects of oxygen supply and demand on hypoxic fraction in tumors. Acta Oncol 1995; 34:313-6.

Segal ED, et al. Relevance of the OCT1 transporter to the antineoplastic effect of biguanides. Biochem Biophys Res Commun 2011; 414:694-9.

Shackelford DB, et al. LKB1 inactivation dictates therapeutic response of non-small cell lung cancer to the metabolism drug phenformin. Cancer Cell 2013; 23:143-58.

Sinnett-Smith J, et al. Metformin inhibition of mTORC1 activation, DNA synthesis and proliferation in pancreatic cancer cells: dependence on glucose concentration and role of AMPK. Biochem Biophys Res Commun 2013; 430:352-7.

Song CW, et al. Metformin kills and radiosensitizes cancer cells and preferentially kills cancer stem cells. Sci Rep 2012; 2:362.

Trumbull KA et al., Diapocynin and apocynin administration fails to significantly extend survival in G93A SOD1 ALS mice. Neurobiol Ois45:137-44, 2012.

Wang J, et al. Synergistic effect of phenformin in non-small cell lung cancer (NSCLC) ionizing radiation treatment. Cell Biochem Biophys 2015; 71(2):513-8.

Weinberg F, et al. (2010) Mitochondrial metabolism and ROS generation are essential for Kras-mediated tumorigenicity. Proc Natl Acad Sci U S A 2010; 107(19):8788-93.

Wendt MK, et al. 2008. Epigenetic silencing of CXCL12 increases the metastatic potential of mammary carcinoma cells. Oncogene, 27(10):1461-71.

Zannella VE, et al. Reprogramming metabolism with metformin improves tumor oxygenation and radiotherapy response. Clin Cancer Res 2013; 19:6741-50.

Notice of the First Office Action in Chinese Application No. 201580055683.3, dated Apr. 26, 2019 (23 pages).

\* cited by examiner

Figure 1A-B

Figure 4
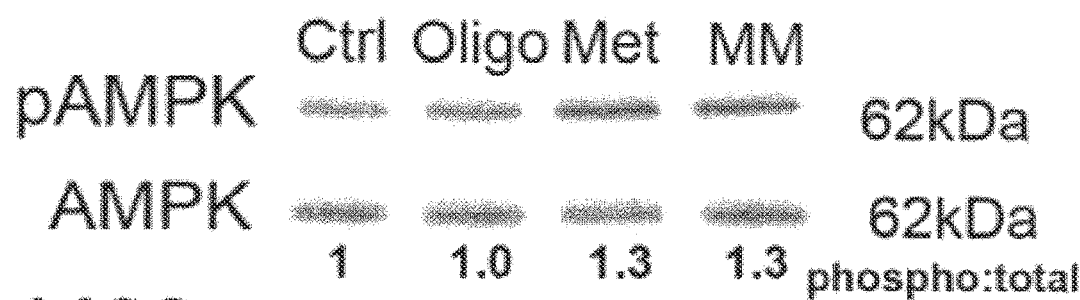
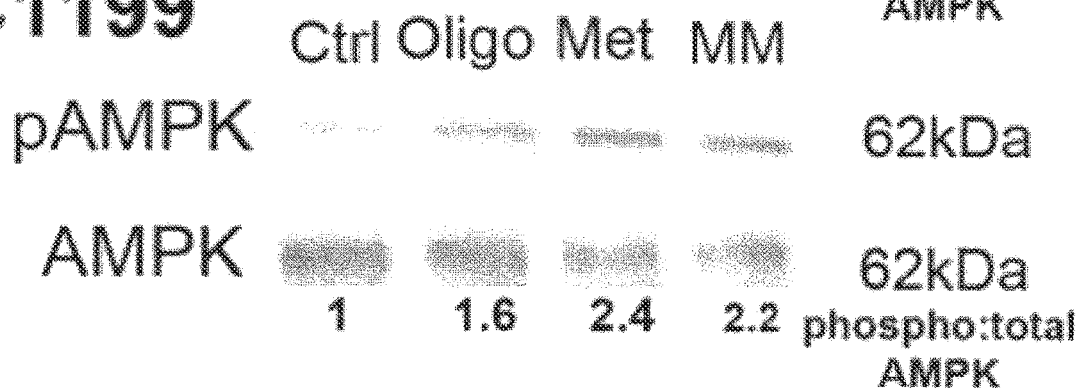

Figure 5A-B

Figures 10A-D
A 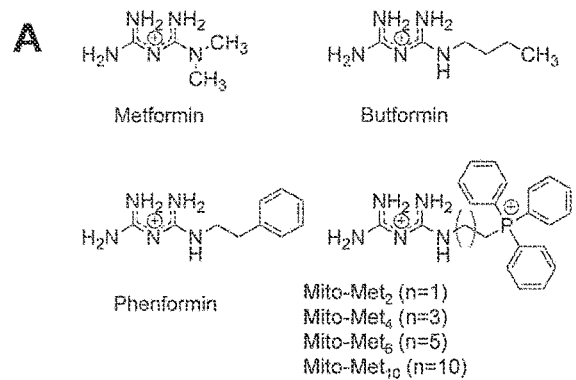
B 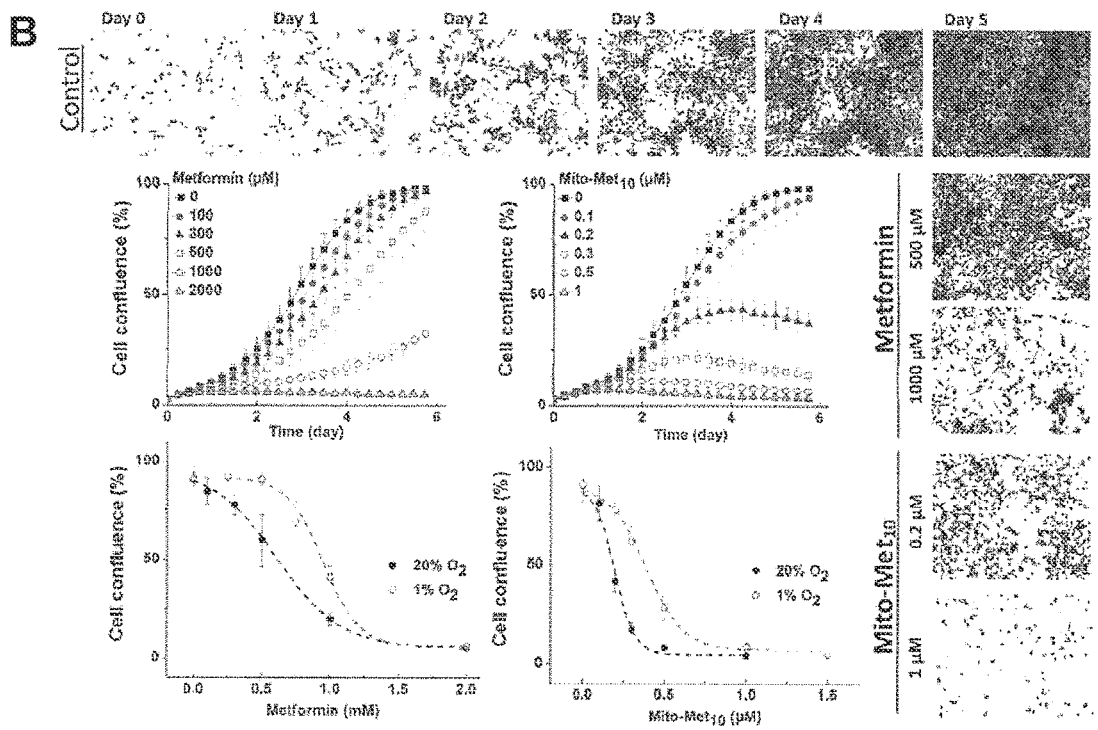
C 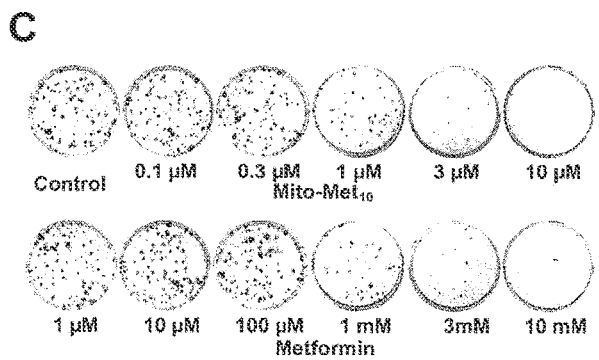
D 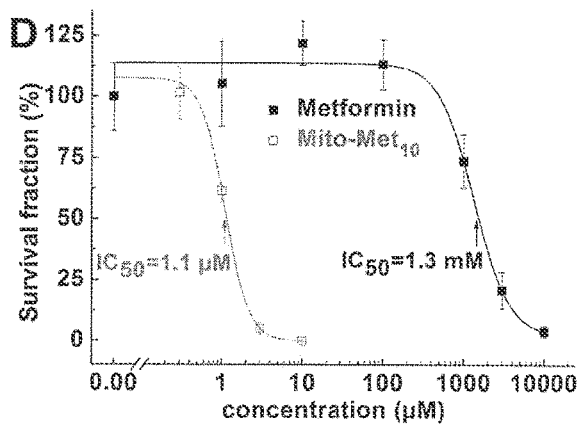

Figure 11A-B
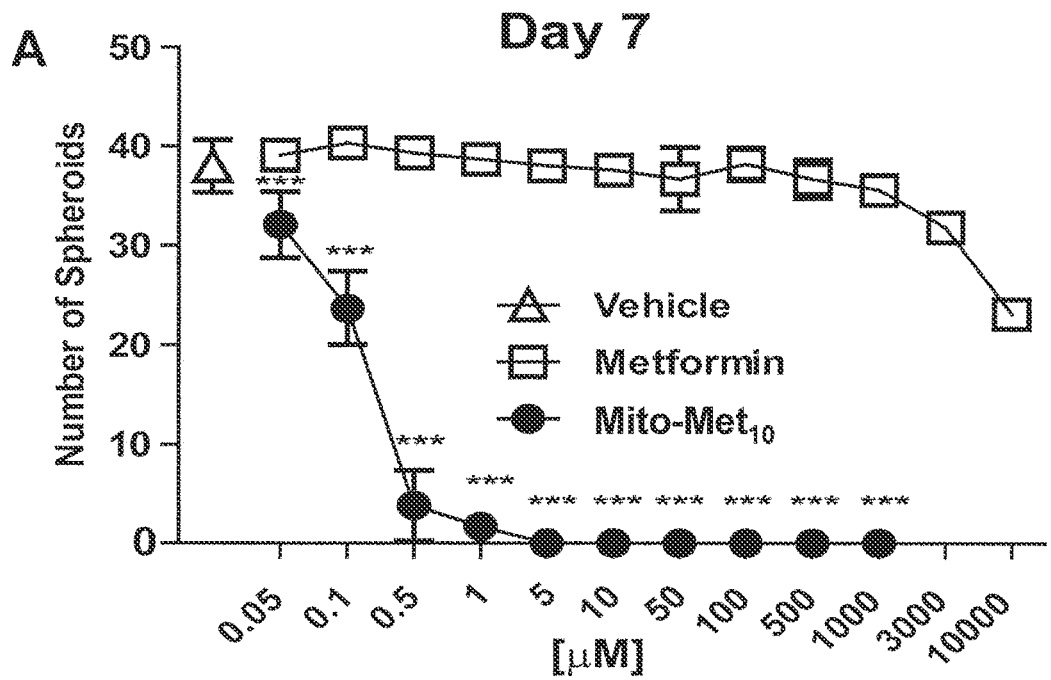
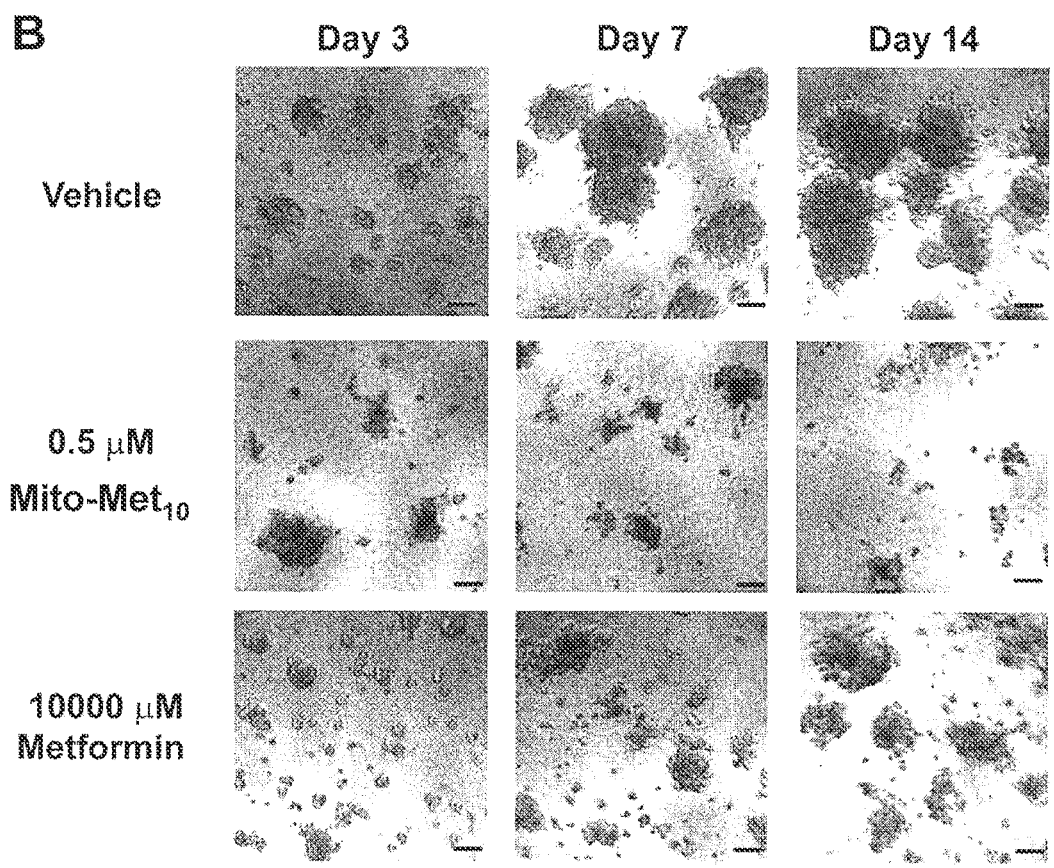

Figure 12A-D
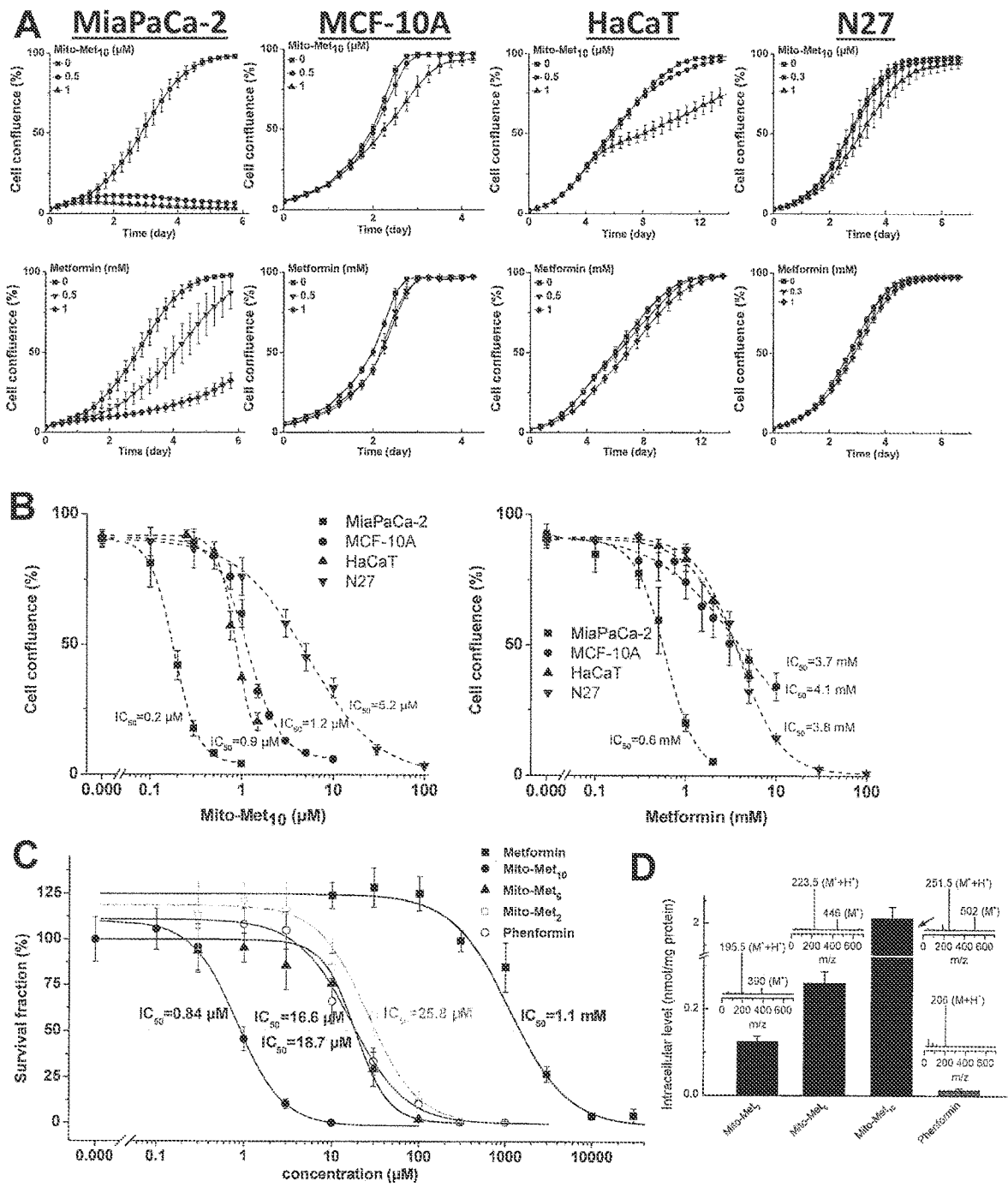

Figure 13A-B
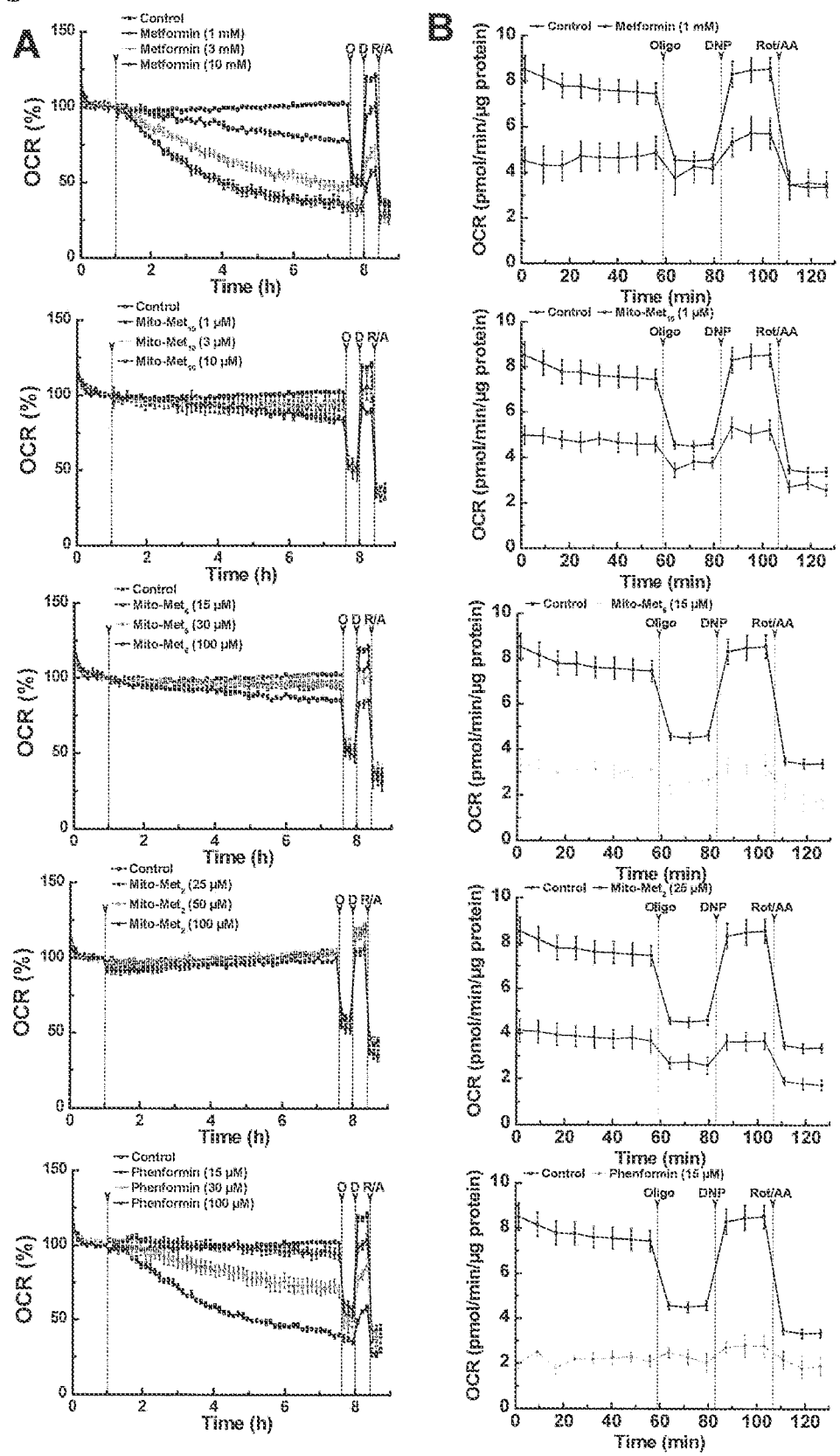

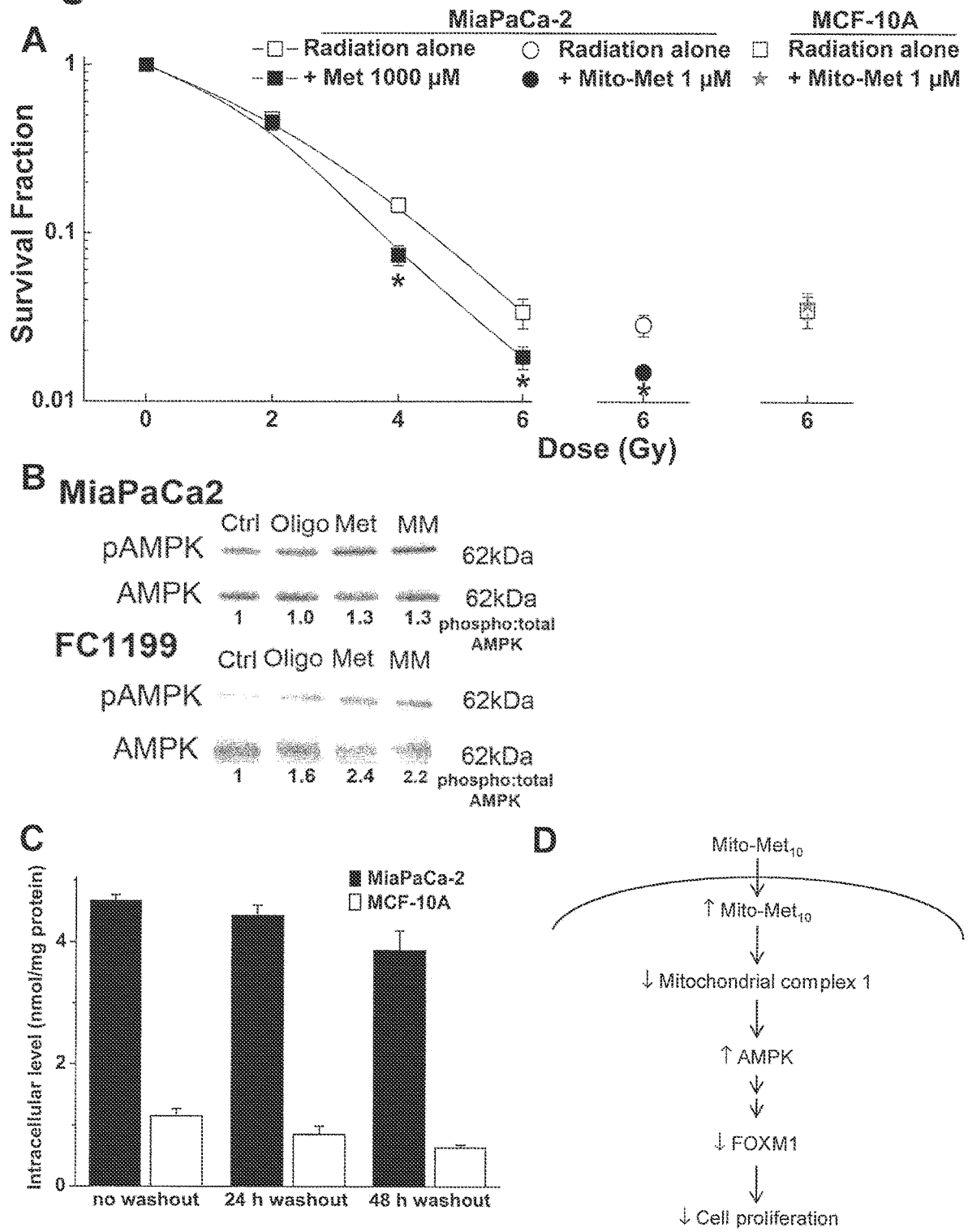
Figure 14A=D

Figure 15A-G
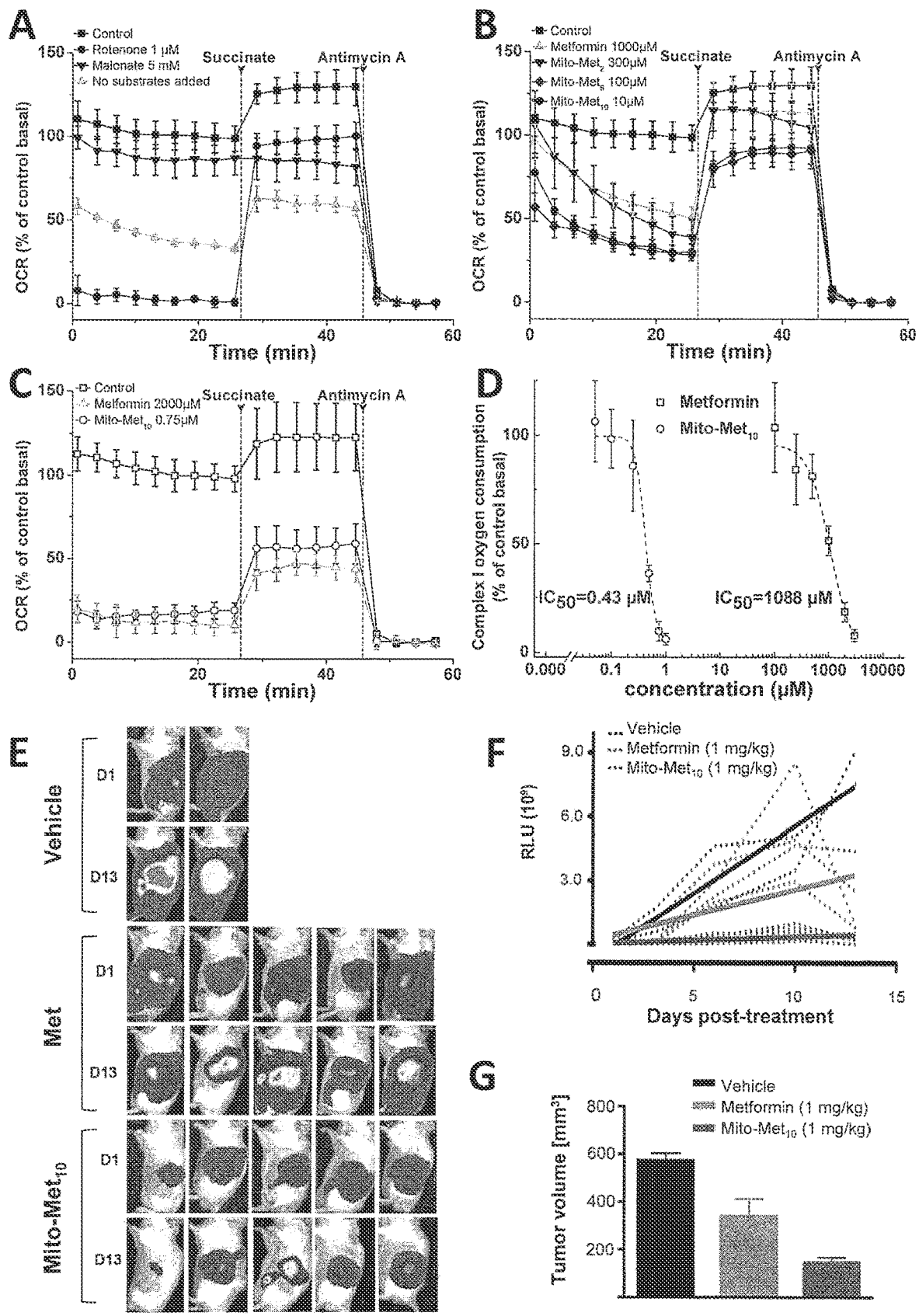

Figure 16A-D
A 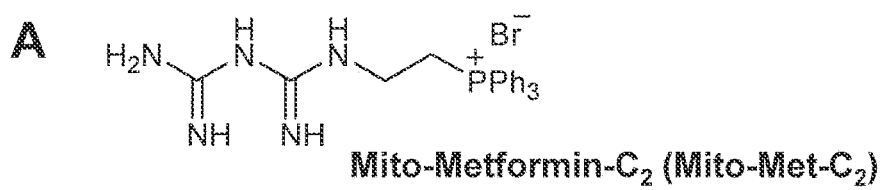
Mito-Metformin-$C_2$ (Mito-Met-$C_2$)
B 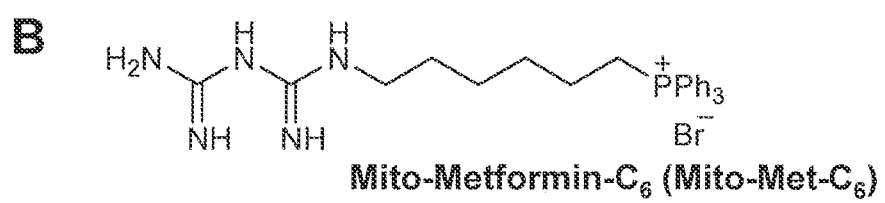
Mito-Metformin-$C_6$ (Mito-Met-$C_6$)
C 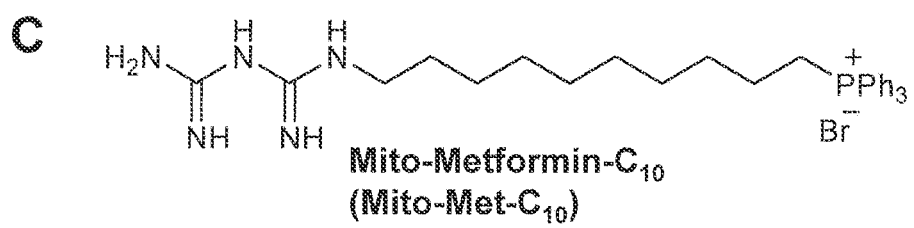
Mito-Metformin-$C_{10}$ (Mito-Met-$C_{10}$)
D 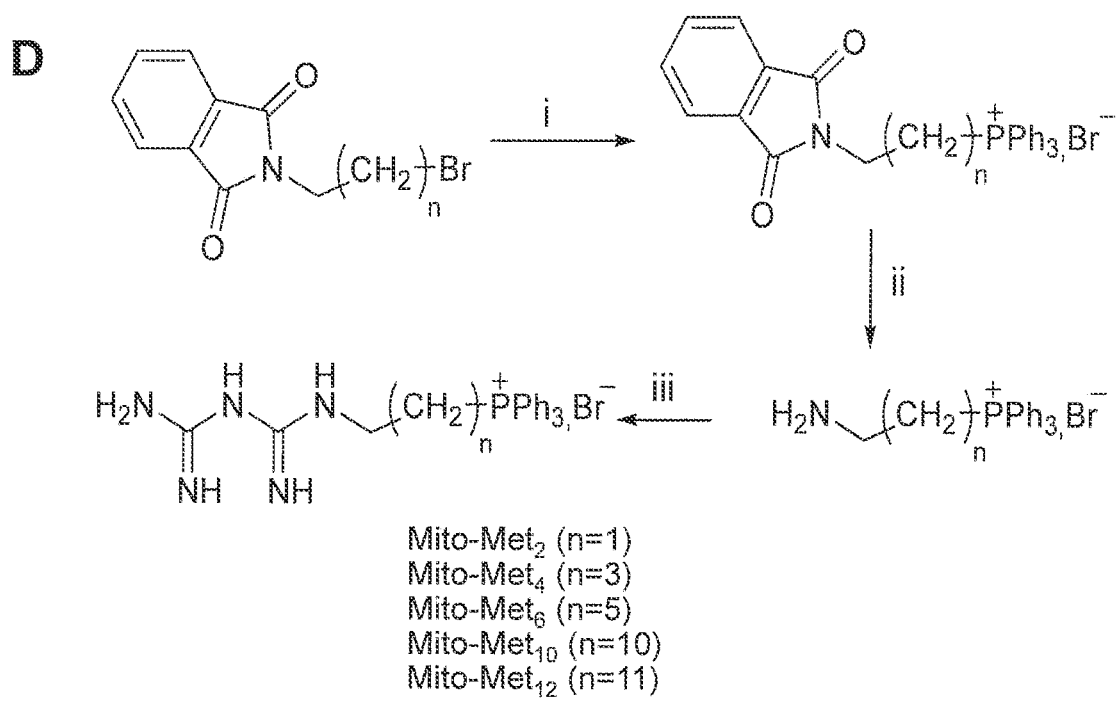
Mito-Met$_2$ (n=1)
Mito-Met$_4$ (n=3)
Mito-Met$_6$ (n=5)
Mito-Met$_{10}$ (n=10)
Mito-Met$_{12}$ (n=11)

Figure 17A-C
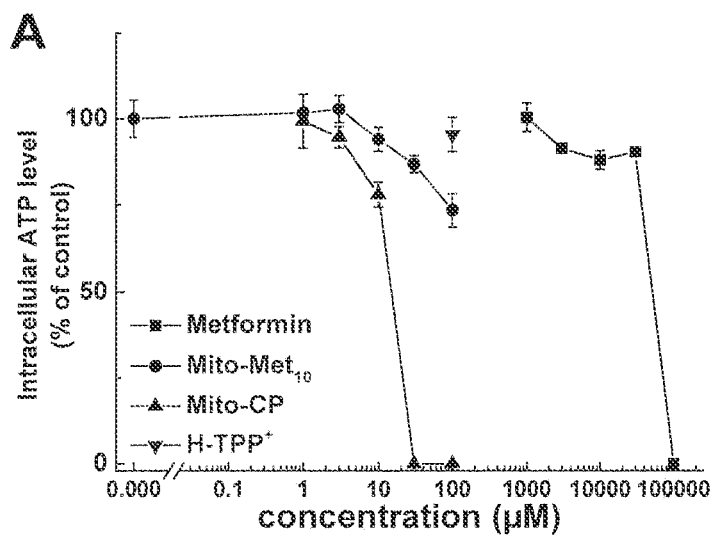
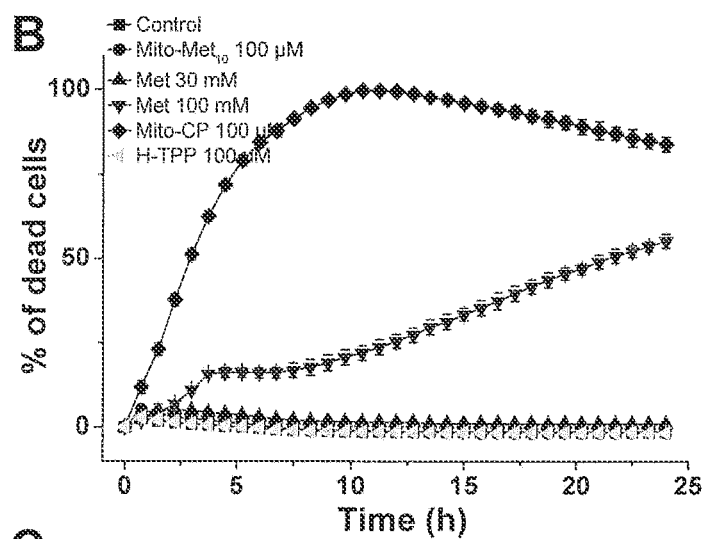
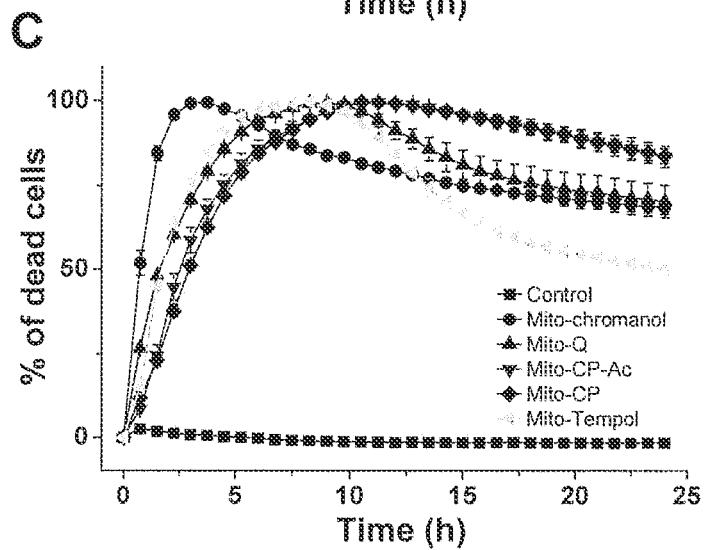

Figure 18A-B
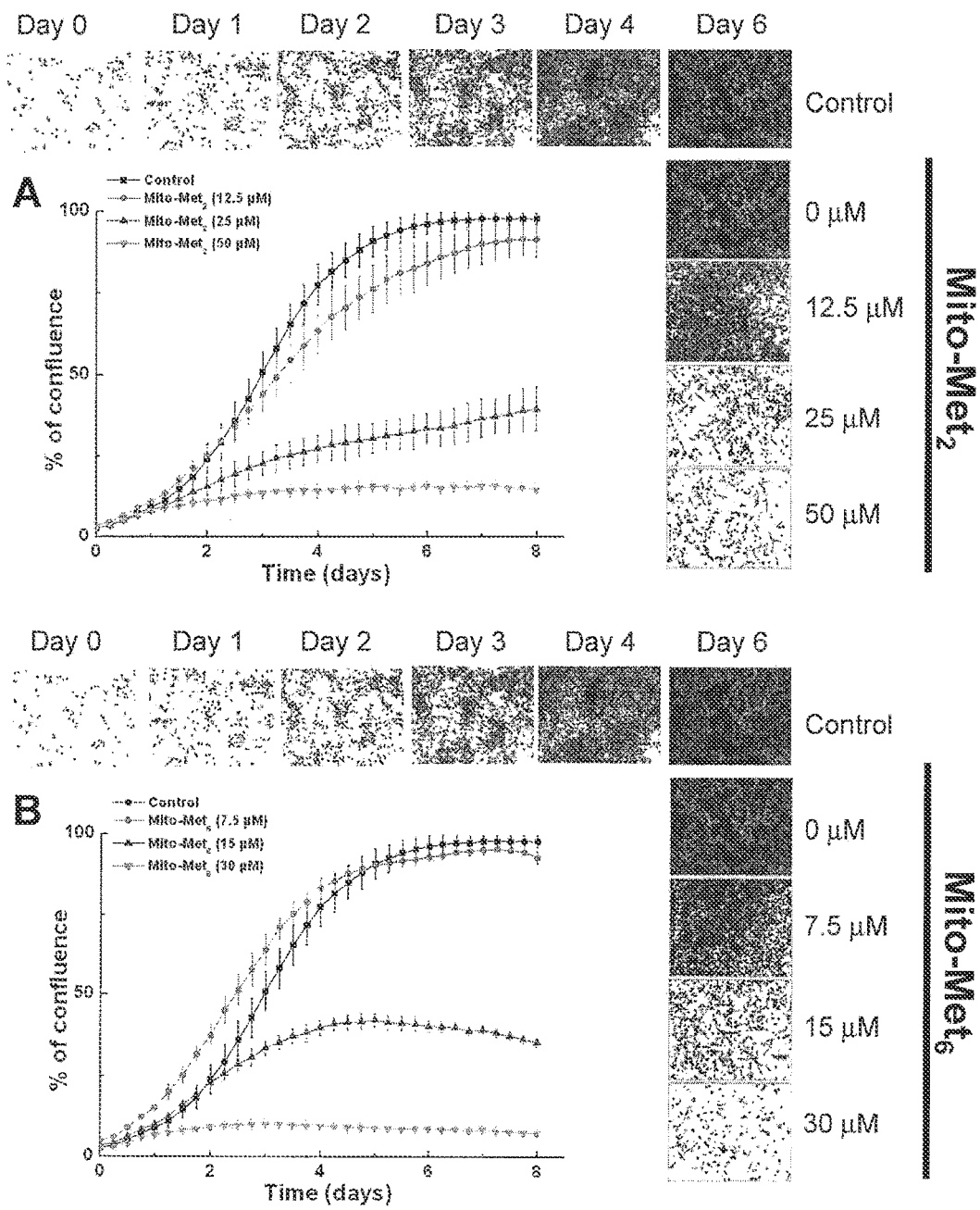

Figure 20A-C

Figure 23A-B
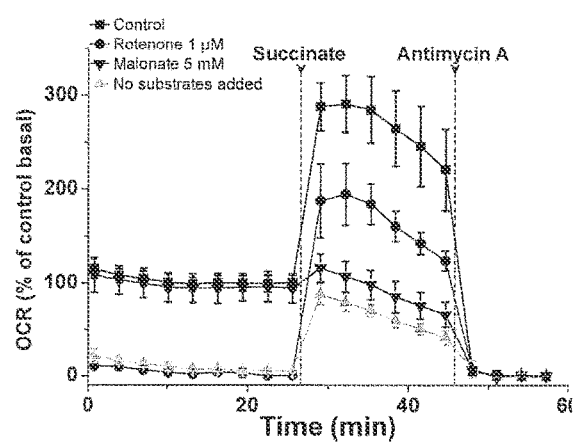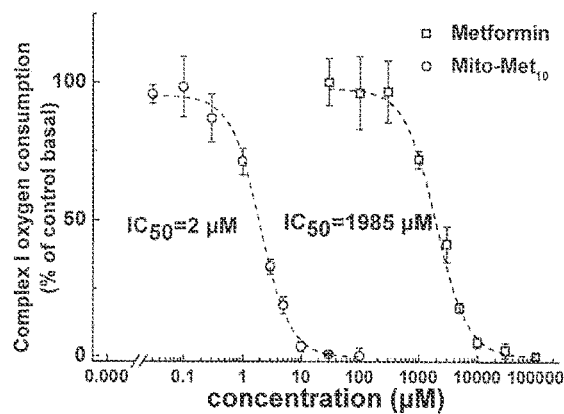

MODIFIED MITO-METFORMIN COMPOUNDS AND METHODS OF SYNTHESIS AND USE THEREOF

CROSS-REFERENCE TO RELATED APPLICATIONS

This application is the U.S. National Phase entry of PCT International Application No. PCT/US2015/045075 filed Aug. 13, 2015 which claims priority to U.S. Provisional Application 62/037,143 filed Aug. 14, 2014, both of which are fully incorporated by reference in their entireties for all purposes.

STATEMENT REGARDING FEDERALLY SPONSORED RESEARCH OR DEVELOPMENT

Not Applicable.

FIELD OF THE INVENTION

This invention relates generally to mitochondria-targeting cationic drugs, specifically to mito-metformin compounds, and methods of using the mito-metformin compounds to treat cancer.

BACKGROUND

Metformin, a biguanide from Galega officinalis, is an FDA-approved drug for treating diabetes (9, which inhibits hepatic gluconeogenesis. Metformin exists as a hydrophilic cation at physiological pH and targets mitochondria, albeit rather inefficiently. Metformin has been in use in the clinic for over 50 years and has a very good safety profile (diabetic patients tolerate daily doses of 2-3 grams). However, little is known about its antitumor mechanism of action, and its molecular target(s) still remain unclear. A prevailing view is that metformin's antitumor and antidiabetic effects are due to its ability to sequester into mitochondria and activate the "AMPK/mTOR pathway", a critical pathway involved in regulating cellular metabolism, energy homeostasis, and cell growth.

Previous attempts to improve and enhance the efficacy of metformin have involved increasing its hydrophobicity through attaching alkyl or aromatic groups (butformin, phenformin). However, these previous efforts have resulted in significant negative side effects, and have not been successful.

Therefore, a need exists for compounds that are effective in inhibiting tumor formation (i.e., reducing the severity or slowing the progression of symptoms of cancer) which have increased efficacy at lower doses while also mitigating resistance to chemo and radiotherapies.

SUMMARY OF THE INVENTION

In one embodiment, the invention comprises a modified metformin compound selected from the group consisting of mito-metformin, mito-phenformin, mito-PEG-metformin, mito-cy-metformin or pyrformin.

In one embodiment, the invention comprises a mito-metformin (mito-met) compound according to the following structure:

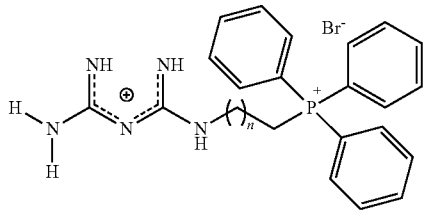

n=1—Mito-Metformin-$C_2$

5—Mito-Metformin-$C_6$

9—Mito-Metformin-$C_{10}$

11—Mito-Metformin-$C_{12}$

In alternate embodiments, the invention comprises a mito-metformin compound according to the following structure:

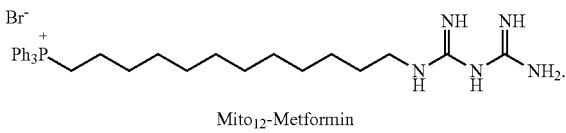

$Mito_{12}$-Metformin

In alternate embodiments, the invention comprises a mito-metformin compound according to the following structure:

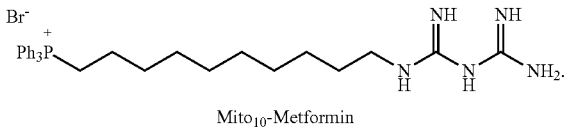

$Mito_{10}$-Metformin

In alternate embodiments, the invention comprises a mito-metformin compound according to the following structure:

$Mito_6$-Metformin

In alternate embodiments, the invention comprises a mito-metformin compound according to the following structure:

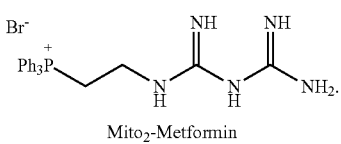

$Mito_2$-Metformin

In alternate embodiments, the invention comprises a mito-metformin compound according to the following structure:

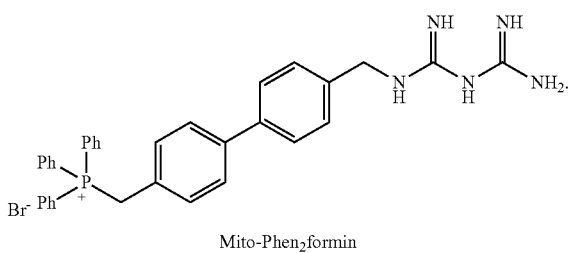

Mito-Phen₂formin

In alternate embodiments, the invention comprises a mito-metformin compound according to the following structure:

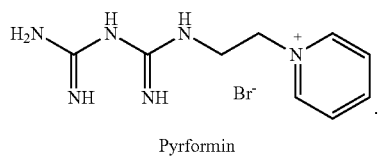

Pyrformin

In alternate embodiments, the invention comprises a mito-metformin compound according to the following structure:

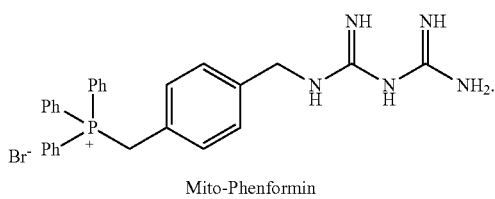

Mito-Phenformin

In alternate embodiments, the invention comprises a mito-metformin compound according to the following structure:

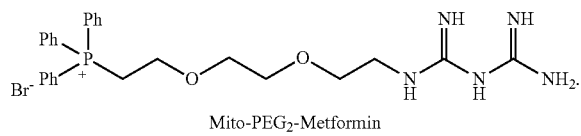

Mito-PEG₂-Metformin

In alternate embodiments, the invention comprises a mito-metformin compound according to the following structure:

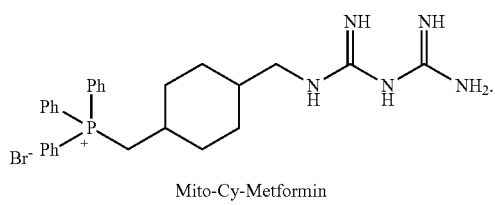

Mito-Cy-Metformin

In alternate embodiments, the invention also comprises a method of inhibiting tumor formation in a subject comprising administering to the subject a therapeutically effective amount of a composition comprising at least one mito-metformin compound as described above.

In alternate embodiments, the invention comprises a kit comprising at least one mito-metformin compound as described above, a pharmaceutically acceptable carrier or diluent, and instructional material.

In alternate embodiments, the invention comprises a kit comprising at least one mito-metformin compound as described above, a pharmaceutically acceptable carrier or diluent, and instructional material.

Other features of the present invention will become apparent after review of the specification, claims and drawings.

BRIEF DESCRIPTION OF THE DRAWINGS

FIG. 4. AMPK activation in mito-metformin-treated PDAC cells. Immunoblot of phosphorylated (p) and total AMPK in MiaPaCa2 (top) and murine FC1199 (bottom) cells. Cells were unstimulated (Ctrl) or treated 30 min with either 1 μM mito-metformin (MM), 1 mM Met, or 1 μg/ml oligomycin (Oligo) as a positive control. Data are representative of 3 biological replicates.

FIG. 10A-D. Effects of Metformin and Mito-Metformin on PDAC proliferation. (A) Chemical structures of metformin and analogs. (B) Effects of Mito-Met$_{10}$ and Metformin on PDAC proliferation. MiaPaCa-2 cells were treated with Mito-Met$_{10}$ (0-1 µM) or Metformin (0-2,000 µM) and cell growth monitored continuously until the end of each experiment using the IncuCyte plate reader (Day 0-Day 6). Changes in cell confluence were used as a surrogate marker of cell proliferation. Dose response of Met (left) or Mito-Met$_{10}$ (right) on cell confluence. Age-matched cells were cultured in three passages in either 20% or 1% oxygen immediately prior to treatment. (C) Effects of Mito-Metformin and Metformin on colony formation in MiaPaCa-2 cells. MiaPaCa-2 cells were treated with Mito-Met$_{10}$ (0.1-10 µM) or Metformin (1 µM-10 mM) for 24 h and the colonies formed were counted. (D) Titration of MiaPaCa-2 cells with Mito-Met$_{10}$ (0.1-10 µM) or Metformin (1 µM-10 mM), and the survival fraction calculated under the same conditions as above is plotted against concentration. Solid lines represent the fitting curves used for determination of the IC$_{50}$ values for cell survival. Data in (A) are representative of 6 independent studies. Values are the mean±SD (n=6).

FIG. 11A-B. Effects of Mito-Met10 and Metformin on PDAC spheroid growth. (A) MiaPaCa-2 cell 3D spheroids were treated with varying concentrations of Mito-Met10 or Met every other day with fresh medium. Values are the mean±SD (n=4). ***=P≤0.001. (B) Representative images of MiaPaCa-2 treated with 0.5 µM Mito-Met10 or 10 mM Metformin at days 3, 7 and 14. PDAC spheroids without treatment (vehicle) are also shown. Scale bars: 100 µm.

FIG. 12A-D. Effects of Metformin and Mito-Met$_{10}$ on pancreatic cancer cell and normal cell proliferation: Cellular uptake of metformin analogs by human pancreatic cancer cells. (A) Effects of Mito-Met$_{10}$ (top) and Metformin (bottom) on proliferation under the same conditions as FIG. 10B. MiaPaCa-2, MCF-10A, and HaCaT cells were treated with Mito-Met$_{10}$ or Metformin and cell growth monitored continuously until the end of each experiment using the IncuCyte. (B) The percentage of cell confluence (as control group reach 90% confluency) is plotted against concentration. Dashed lines represent the fitting curves used to determine the IC$_{50}$ values. (C) MiaPaCa-2 cells were treated with Mito-Met analogs with different carbon chain lengths (Mito-Met$_2$, Mito-Met$_6$ and Mito-Met$_{10}$), metformin or phenformin for 24 h and the colonies formed were counted. The calculated survival fraction is plotted against concentration. Solid lines represent the fitting curves used for determination of the IC$_{50}$ values. Data shown represent the mean±SD, (n=6). (D) Cellular uptake of the biguanide phenformin and Mito-Met analogs with different carbon chain lengths (Mito-Met$_2$, Mito-Met$_6$, and Mito-Met$_{10}$) was quantified using LC-MS/MS. Values are mean±SD, n=3.

FIG. 13A-B. Effects of Met, Mito-Met analogs and phenformin on mitochondrial bioenergetics observed immediately and after 24 h treatment in MiaPaCa-2 cells. (A) Oxygen consumption rate (OCR) measured immediately after addition of Met, Mito-Met analogs (Mito-Met$_{10}$, Mito-Met$_6$, Mito-Met$_2$) and Phenformin, and (B) OCR measured after 24 h under the same conditions as (A).

FIG. 14A-D. Colony formation assay of MiaPaCa-2 cells or normal MCF-10A cells treated with radiation alone or with metformin (Met) analogs and AMPK activation in Mito-Metformin-treated PDAC cells. (A) Cells were treated with 1,000 µM Met (left) or 1 µM Mito-Met$_{10}$ (middle and right) 24 h before ionizing radiation (0-6 Gy) and clonogenic survival fraction were determined. Colonies were allowed to form in medium without treatment for 14 days. Values are the mean±SD. *, P≤0.05 (n=6 independent experiments) compared to control compared to radiation dose. (B) Immunoblot of phosphorylated (p) and total AMPK in MiaPaCa-2 (top) and murine FC1199 (bottom) cells. Cells were unstimulated (Ctrl) or treated 30 min with either 1 µM Mito-Metformin (MM), 1 mM Met, or 1 µg/ml oligomycin (Oligo) as a positive control. Data are representative of 3 biological replicates. (C) Intracellular retention of Mito-Met$_{10}$ in tumor and normal cells. (D) The proposed model showing how Mito-Met$_{10}$ inhibits PDAC proliferation via decreased complex I activity.

FIG. 15A-G. Mito-Met and Metformin inhibit pyruvate-driven, but not succinate-driven, respiration and Mito-Met$_{10}$ potently inhibits tumor growth and progression in vivo. (A), and (B) Representative experiment of permeablized MiaPaCa-2 cells offered 10 mM pyruvate and 1.5 mM malate in MAS buffer. Either rotenone, malonate or Mito-Met$_{10}$, Mito-Met$_6$, Mito-Met$_2$, and metformin were added acutely and OCR was assayed immediately. (C) Cells were pretreated with Metformin or Mito-Met$_{10}$ for 24 h before the assay. (D) the mitochondrial complex I oxygen consumption (last OCR reading before succinate injection) is plotted against concentration. Dash lines represent the fitting curves used for determination of the IC$_{50}$ values. Both succinate (10 mM) and antimycin A (20 µM) were injected where indicated. Data shown are the mean±SD, n=4. (E) Whole body bioluminescence imaging showing decreased tumor growth in Mito-Met$_{10}$ (1 mg/kg) treated mice relative to Met (1 mg/kg) treated mice. (F) Total bioluminescence values (Radiance luminescence unit, RLU) for individual FC1242-luc autografts. Dotted lines represent individual mice. Solid lines are quadratic regression fitted curves for vehicle (black line), Met$_{10}$ (red line) or Mito-Met (blue line) treated animals. (G) Tumor volume measured using calipers of excised primary FC1242 tumors. Data are values ±SD.

FIG. 16A-D. Synthesis of (A) Mito-Metformin-C$_2$. A 0.1 g portion of (2-Aminoethyl) triphenylphosphonium Bromide (0.26 mmol) was dissolved in CH$_2$Cl$_2$ (3 mL) and the mixture was cooled to 0° C. A 336 µL portion of 1.0 M solution of HCl in diethyl ether (0.33 mmol) was added dropwise. After 90 min at room temperature, the solvent was removed under vacuum. Sodium dicyanamide (0.026 g, 0.31 mmol) was added in BuOH (3 mL). The mixture was heated to reflux overnight, after which the solvent was evaporated and the residue was purified by HPLC to give Mito-Metformin$_2$ 1 1(0.030 g, 25%). $^{31}$P NMR, (600.13): δ 21.61. $^1$H NMR, (600.13 MHz): δ 7.93-7.73 (15H, m), 3.80-3.76 (2H, m), 3.38-3.34 (2H, m). $^{13}$C NMR (75.47 MHz) λ 158.3 (s), 158.1 (s), 135.1 (s), 133.7 (s), 133.6 (s), 130.3 (s), 131.2 (s), 117.6 (d, J=85), 35.1 (s), 20.6 (d, J=47). HRMS calculated for C$_{22}$H$_{25}$N$_5$P [C$_{22}$H$_{25}$N$_5$P]$^+$ 390.1842, found 390.1842. (B) Mito-Metformin-C$_6$. A 0.1 g portion of (6-Aminohexyl) triphenylphosphonium Bromide (0.23 mmol) was dissolved in CH$_2$Cl$_2$ (3 mL) and the mixture was cooled to 0° C. A 453 µL portion of 1.0 M solution of HCl in diethyl ether (0.45 mmol) was added dropwise. After 90 min at room temperature, the solvent was removed under vacuum. Sodium dicyanamide (0.028 g, 0.33 mmol) was added in BuOH (3 mL). The mixture was heated to reflux overnight, after which the solvent was evaporated and the residue was purified by HPLC to give Mito-Metformin$_6$ (0.020 g, 17%). $^{31}$P NMR, (600.13): δ 24.6. $^1$H NMR, (600.13 MHz): δ 7.93-7.88 (3H, m), 7.81-7.77 (12H, m), 3.60-3.46 (2H, m), 3.05-3.00 (2H, m), 1.55-1.48 (2H, m), 1.48-1.42 (2H, m), 1.41-1.35 (2H, m), 1.31-1.24 (2H, m).$^{13}$C NMR (75.47 MHz) δ 158.2 (s), 157.9 (s), 134.9 (s), 133.6 (s), 133.5 (s), 130.3 (s), 130.2 (s), 118.2 (d, J=86), 40.0 (s), 30.0 (s), 29.5 (s), 25.9 (s), 22.2 (d, J=3), 20.5 (d, J=49). HRMS calculated for $C_{26}H_{33}N_5P$ $[C_{26}H_{33}N_5P]^+$ 446.2468, found 446.2467. (C) Mito-Metformin-$C_{10}$. A 0.2 g portion of (10-Aminodecyl) triphenylphosphonium Bromide 2 (0.4 mmol) was dissolved in $CH_2Cl_2$ (3 mL) and the mixture was cooled to 0° C. A 500 µL portion of 1.0 M solution of HCl in diethyl ether (0.5 mmol) was added dropwise. After 1 h at room temperature, the solvent was removed under vacuum and dicyandiamide (0.034 g, 0.4 mmol) was added in BuOH (2 mL). The mixture was heated to reflux overnight, after which the solvent was evaporated and the residue was purified by HPLC to give Mito-Metformin$_{10}$ 3 (0.060 g, 30%). $^{31}$P NMR, (400.13): δ 23.77. $^1$H NMR, (400.13 MHz): δ 7.91-7.73 (15H, m), 3.42-3.33 (2H, m), 3.25-3.20 (2H, m), 1.69-1.51 (6H, m), 1.40-1.21 (10H, m). HRMS calculated for $C_{30}H_{41}N_5P$ $[C_{30}H_{41}N_5P]^+$ 502.3094, found 502.3094.

FIG. 17A-C. The effects of Mito-Met$_{10}$, metformin and other MTAs on intracellular ATP levels and cell death in MiaPaCa-2 cells. MiaPaCa2 cells were treated as indicated. (A) Intracellular ATP level is plotted against concentration after 24 h treatment. (B,C) Cell death was monitored in real time by Sytox Green staining for 24 h and real time cell death curves were plotted. Data shown are the means±SD for n=4.

FIG. 18A-B. Effects of Mito-Metformin-$C_2$ and Metformin (control) on PDAC proliferation. (A) MiaPaCa2 cells were treated with Mito-Metformin-$C_2$ (µM) or metformin (mM) and cell growth monitored continuously until the end of each experiment using the IncuCyte plate reader (Day 0-Day 6). Changes in cell confluence were used as a surrogate marker of cell proliferation. Values are the mean±SD (n=6). (B) Effects of Mito-Metformin-$C_6$ and Metformin (control) on PDAC proliferation. MiaPaCa2 cells were treated with Mito-Metformin-$C_6$ (µM) or Metformin (mM) and cell growth monitored continuously until the end of each experiment using the IncuCyte plate reader (Day 0-Day 6). Changes in cell confluence were used as a surrogate marker of cell proliferation. Values are the mean±SD (n=6).

FIG. 23A-B. Mito-Met and Metformin inhibit pyruvate-driven, but not succinate-driven, respiration in N27 cells. (A) Representative experiment of permeablized N27 cells containing 10 mM pyruvate and 1.5 mM malate in MAS buffer. Experimental conditions are the same as shown in FIG. 15A-G. (B) Metformin or Mito-Met$_{10}$ were pretreated for 24 h before the assay. The mitochondrial complex I oxygen consumption (last OCR reading before succinate injection) is plotted against concentration. Dash lines represent the fitting curves used for determination of the IC$_{50}$ values. Data shown are the mean±SD, n=4.

DETAILED DESCRIPTION OF THE INVENTION

Figure 1:
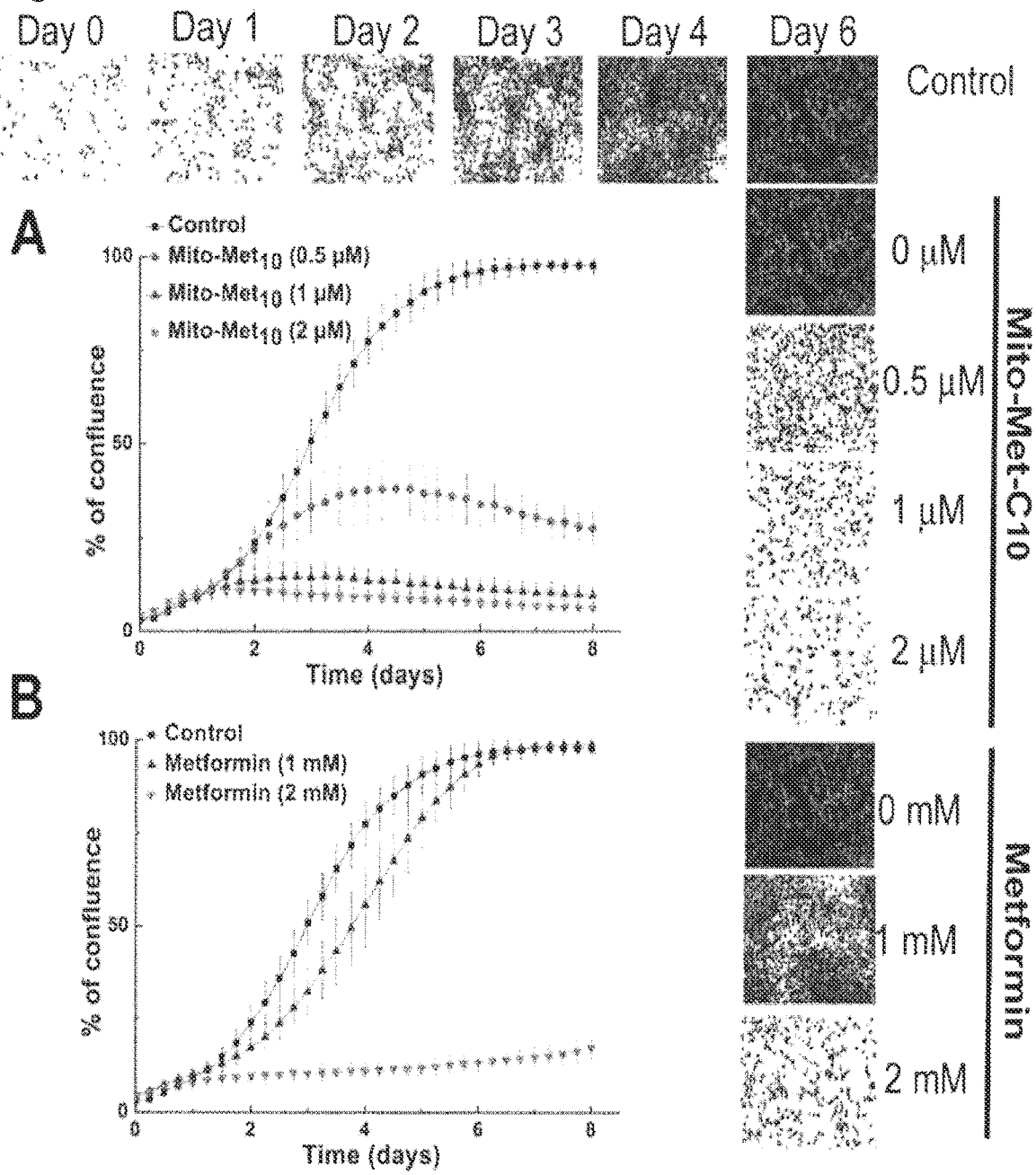
FIG. 1A-B. Effects of mito-meformin-C10 and metformin (control) on PDAC proliferation. MiaPaCa2 cells were treated with mito-metformin-C10 (μM) (A) or metformin (mM) (B) and cell growth monitored continuously until the end of each experiment using the IncuCyte plate reader (Day 0-Day 6). Changes in cell confluence were used as a surrogate marker of cell proliferation. Values are the mean±SD (n=6).

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention. In one embodiment, the present invention provides novel mito-metformin (mito-met) compounds modified to selectively and synergistically inhibit cancer proliferation and progression. Specifically, the inventors have shown that attaching a positively-charged group to metformin greatly enhances the compounds antitumor efficacy at very low doses when compared to conventional treatments.

In one embodiment, the mito-met compounds of the present invention comprise metformin modified to include alkyl cationic moieties. In other embodiments, the mito-met compounds of the present invention comprise a metformin compound selected from the group consisting of phenformin, PEG, cy-metformin or pyrformin.

Specifically, the inventors have shown that mitochondria-targeted metformin analogs (Mito-Mets) are significantly more potent than metformin in inhibiting pancreatic cancer cell proliferation. Metformin (Met) is an FDA-approved antidiabetic drug that is currently being repurposed as a promising antitumor drug. As Met targets mitochondria, although not very effectively, we surmised that increasing its mitochondria targeting potential by attaching a positively-charged lipophilic substituent will result in more potent Mito-Mets with enhanced antitumor potential. To this end, novel Mito-Met analogs conjugated to varying alkyl chain lengths containing a triphenylphosphonium cation (TPP$^+$) were synthesized and characterized. Results show that Mito-Met analog (e.g., Mito-Met$_{10}$) synthesized by attaching TPP$^+$ to Met via a 10-carbon aliphatic side chain is nearly 1,000 times more effective than Met in inhibiting pancreatic ductal adenoma cell (PDAC) proliferation. Mito-Met$_{10}$ was 2,000-fold more effective than Met in inhibiting mitochondrial complex I-mediated oxygen consumption in MiaPaCa-2 cells (IC$_{50}$ for Mito-Met$_{10}$≈0.43 µM and IC$_{50}$ for Met≈1,088 µM). Mito-Met$_{10}$ (1 mg/kg) was considerably more potent than Met in abrogating in vivo tumor growth. Results also show that pretreatment of PDACs with Mito-Met at 1,000-fold lower concentration than Met enhanced radiosensitization, as measured by a clonogenic assay. Enhanced mitochondrial targeting of Met, combined with enhanced radiosensitizing efficacy could be significantly more beneficial in the treatment of pancreatic carcinoma, an aggressive human cancer with limited chemo- or radiotherapeutic options to improve survival.

In one embodiment, the mito-met compounds of the present invention are as follows:

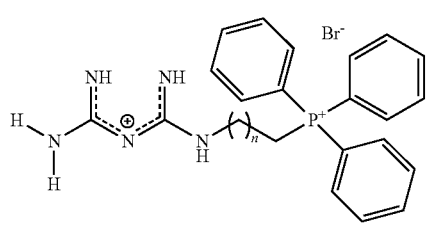

n=1—Mito-Metformin-C$_2$
5—Mito-Metformin-C$_6$
9—Mito-Metformin-C$_{10}$
11—Mito-Metformin-C$_{12}$ In one specific embodiment, the mito-met compound of the present invention comprises the following structure:

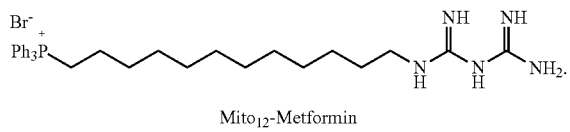

Mito$_{12}$-Metformin

In one specific embodiment, the mito-met compound of the present invention comprises the following structure:

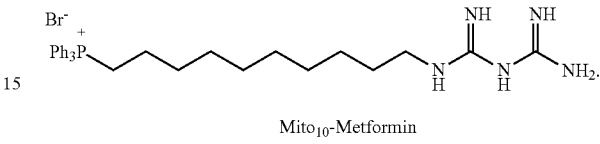

Mito$_{10}$-Metformin

In one specific embodiment, the mito-met compound of the present invention comprises the following structure:

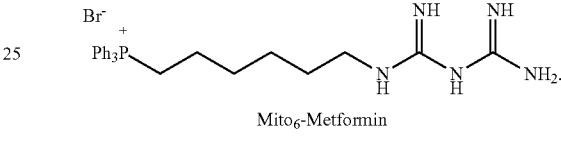

Mito$_6$-Metformin

In one specific embodiment, the mito-met compound of the present invention comprises the following structure:

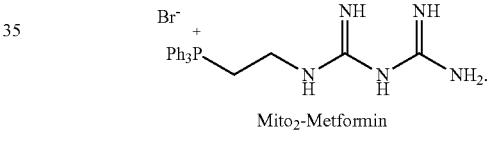

Mito$_2$-Metformin

In one specific embodiment, the mito-met compound of the present invention comprises the following structure:

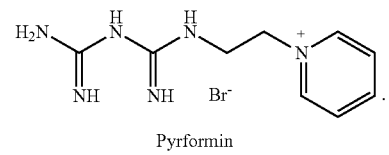

Pyrformin

In one specific embodiment, the mito-met compound of the present invention comprises the following structure:

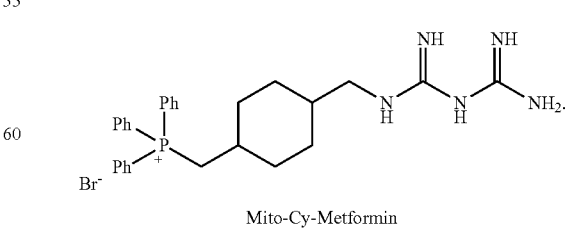

Mito-Cy-Metformin

In one specific embodiment, the mito-met compound of the present invention comprises the following structure:

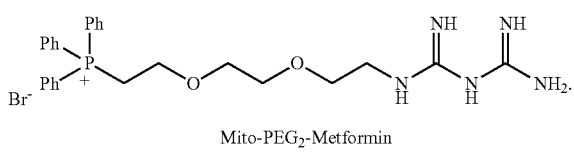

Mito-PEG$_2$-Metformin

In one specific embodiment, the mito-met compound of the present invention comprises the following structure:

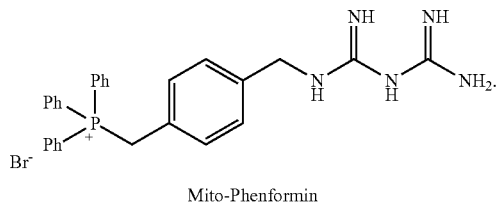

Mito-Phenformin

In one specific embodiment, the mito-met compound of the present invention comprises the following structure:

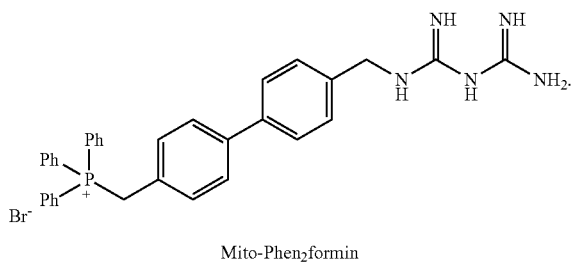

Mito-Phen$_2$formin

Methods of Synthesis. The mito-met compounds of the present invention are prepared by reacting the corresponding aminoalkyltriphenylphosphonium bromide with dicyandiamide at 100-180° C. Subsequently, the product is purified either by flash chromatography or on HPLC.

In one embodiment, the mito-met compounds of the current invention comprise combinations of glycolytic, glutaminolytic, and/or mitochondrial metabolism inhibitors which, with standard therapies, treat cancer.

Methods of Use. In one embodiment, the invention provides a method of treating cancer in a subject comprising administering to the subject a therapeutically effective amount of a composition comprising at least one mito-met compound of the present invention. In one embodiment, the composition comprises one mito-met compound of the present invention, but in alternate embodiments multiple mito-met compounds of the invention may be administered.

In use, the mito-met compounds of the present invention are more cytotoxic to cancer cells than to non-cancerous cells. The inventors have demonstrated that the mito-met-formin compounds of the present invention potently inhibit tumor cell proliferation and induce cytotoxicity by selectively inhibiting tumor, but not normal, cells. In addition, the mito-met compounds of the present invention are more effective at much lower doses than the doses required with conventional treatments using metformin.

Figure 2:
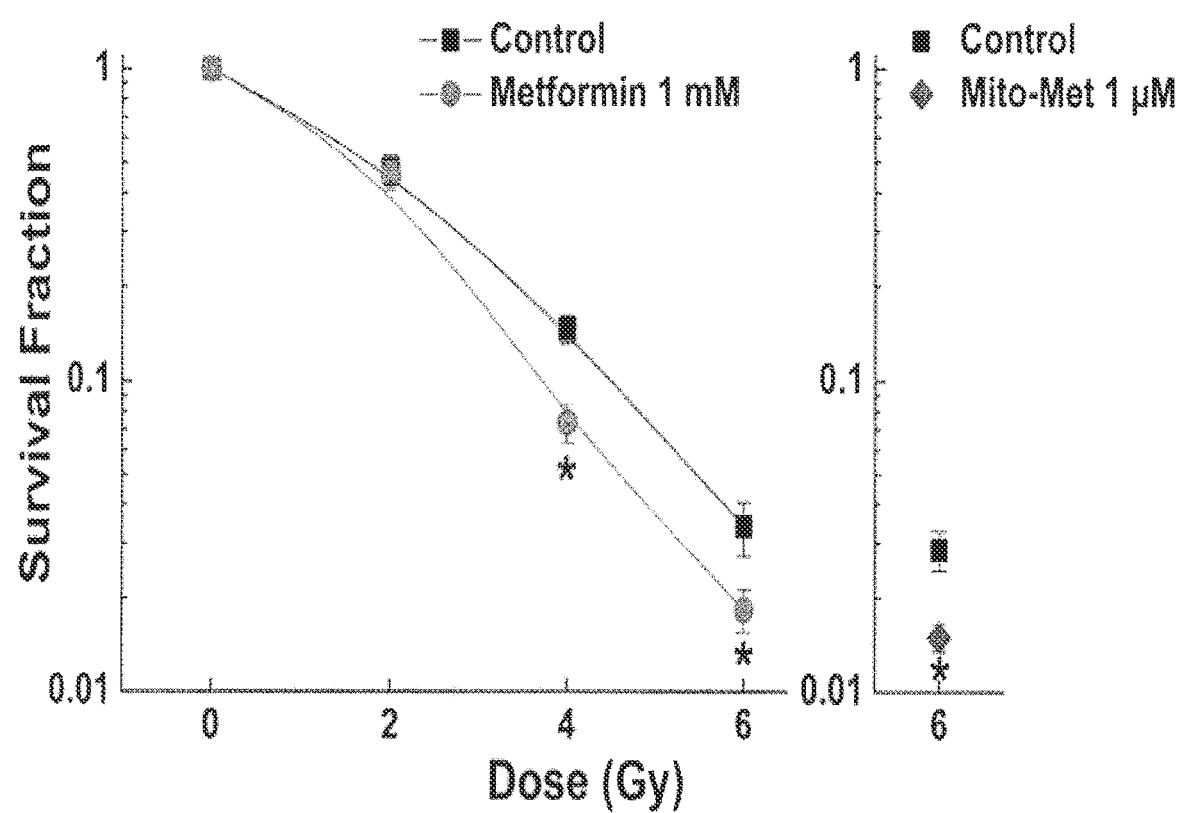
FIG. 2. Colony formation assay of PDAC cells treated with radiation alone or with metformin (Met) analogs. MiaPaCa2 cells were treated with 1 mM Met or 1 μM mito-metformin 24 hr before ionizing radiation (0-6 Gy) and clonogenic survival determined. Colonies were allowed to form in medium without treatment for 14 days. Values are the mean±SD. *, P≤0.05 (n=3-6 independent experiments) compared to control under the same radiation conditions.
Figure 5:
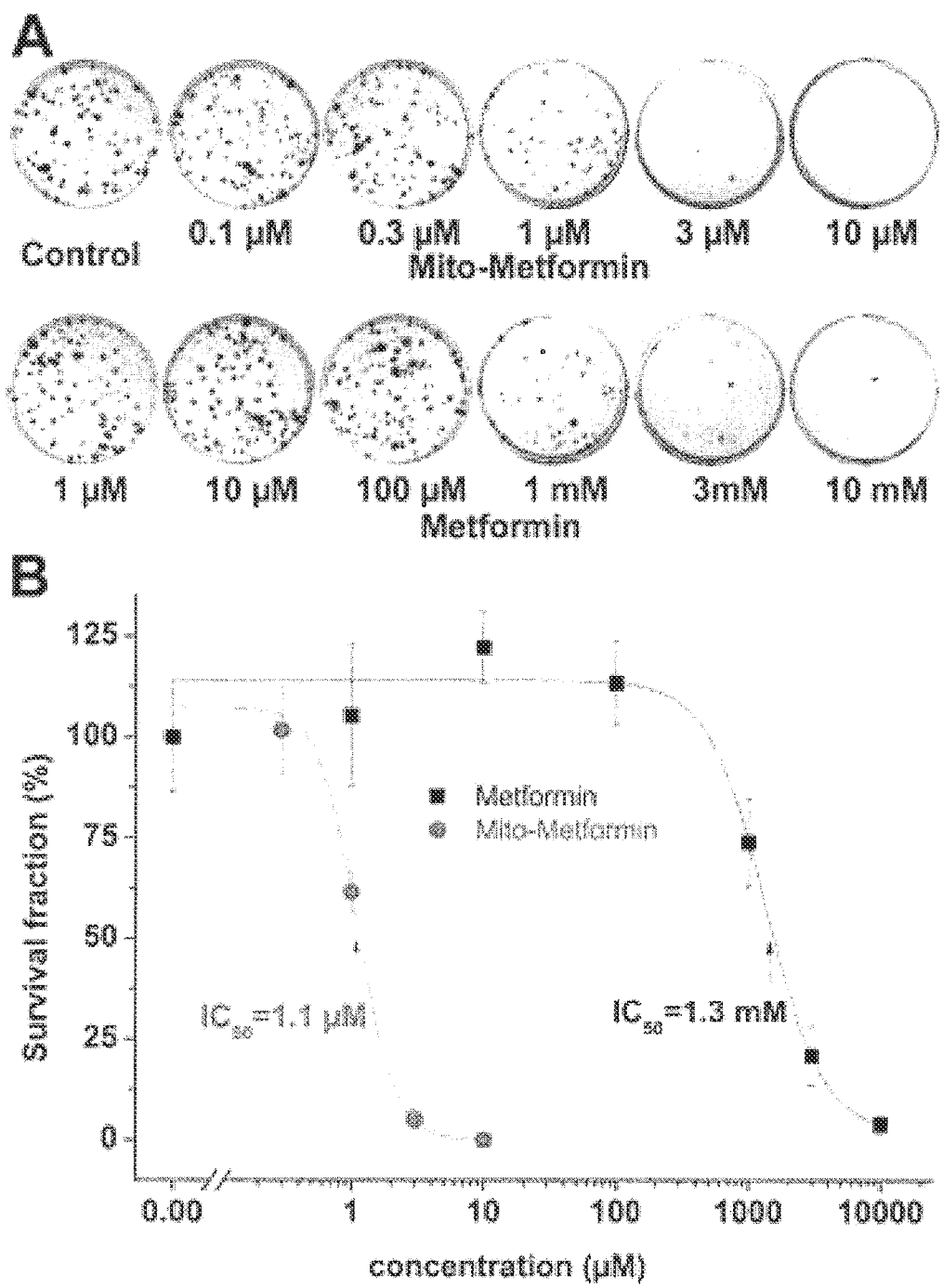
FIG. 5A-B. Clonogenic assay which measures the colony formation in MiaPaCa2 cells after a 24 h treatment with metformin and mito-metformin (C10). Results show that the 1050 values determined for metformin and mito-metformin (C10) were 1.3 mM and 1.1 uM, indicating the mito-met-C10 is nearly 1,000-fold more effective than metformin in inhibiting MiaPaCa-2 cell proliferation.

Specifically, the mito-met compounds of the present invention were nearly 1,000-fold more effective than metformin in inhibiting pancreatic cancer cell proliferation (FIG. 5). In addition, the mito-met compounds of the present invention synergistically enhance radiation-induced pancreatic cancer cell killing at concentrations 1,000-fold less than that of metformin (FIG. 2).

Figure 6:
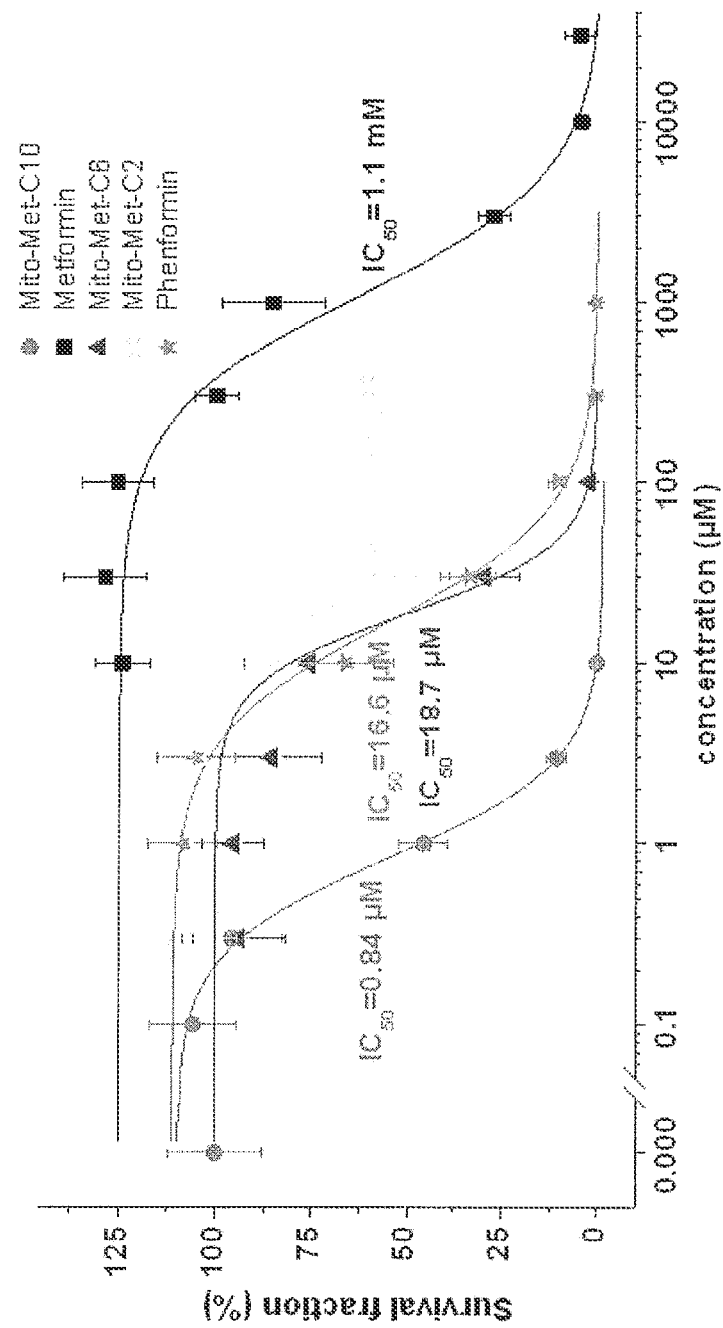
FIG. 6. Clonogenic assay which measures the colony formation in MiaPaCa2 cells after a 24 h treatment with metformin and mito-metformins C10, C6, C2 and Phenformin.

In one embodiment, Mito-Met$_{10}$ (FIG. 10A) is nearly 1,000-fold more effective than Met in inhibiting PDAC proliferation and at least 100 times more effective than Met in abrogating PDAC tumor growth. In other embodiments, Mito-Met$_{10}$ was 2,000-fold more effective than Met in inhibiting mitochondrial complex I-mediated oxygen consumption in MiaPaCa-2 cells (IC$_{50}$ for Mito-Met$_{10}$≈0.43 µM and IC$_{50}$ for Met≈1,088 µM). Mito-Met$_{10}$ (1 mg/kg) was considerably more potent than Met in abrogating in vivo tumor growth. We show that Mito-Met$_{10}$ causes enhancement in radiation sensitivity to the same extent Met (1 mM) but at a 1,000-fold lower concentration (1 µM). This demonstrates that relatively nontoxic mitochondria-targeted metformin analogs alone or in combination with radiotherapy can abrogate pancreas cancer cell proliferation. Further, the mito-met compounds of the present invention are at least 20 times more effective than phenformin (FIG. 6).

The invention also provides therapeutic compositions comprising at least one of the mito-met compounds of the present invention and a pharmacologically acceptable excipient or carrier. The therapeutic composition may advantageously be soluble in an aqueous solution at a physiologically acceptable pH.

In one embodiment, the mito-met compounds of the present invention provide effective methods of treating cancer. In one embodiment, the mito-met compounds of the present invention potently inhibit tumor formation. In other embodiments, the mito-met compounds of the present invention can be combined with ionizing radiation to inhibit tumor cell formation.

In other embodiments, the mito-met compounds of the present invention can, when combined with conventional treatment protocols, increase the effectiveness of conventional cancer treatments.

By "tumor" we mean any abnormal proliferation of tissues, including solid and non-solid tumors. For instance, the composition and methods of the present invention can be utilized to treat cancers that manifest solid tumors such as pancreatic cancer, breast cancer, colon cancer, lung cancer, prostate cancer, thyroid cancer, ovarian cancer, skin cancer, and the like. The composition and methods of the present invention can also be utilized to treat non-solid tumor cancers such as non-Hodgkin's lymphoma, leukemia and the like.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex.

By "treating" we mean the management and care of a subject for the purpose of combating the disease, condition, or disorder. The terms embrace preventative, i.e., prophylactic, and palliative treatments. Treating includes the administration of a compound of the present invention to prevent, ameliorate and/or improve the onset of the symptoms or complications, alleviating the symptoms or complications, or eliminating the disease, condition, or disorder.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the mito-met compounds of the present invention, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the mito-met compounds of the present invention is administered to a subject or is used in an assay or other method described herein or a cited reference, e.g., within about 1 hour of the administration or use of the mito-met compounds of the present invention to about 3, 6, 9 months or more after a subject(s) has received the mito-met compounds of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the mito-met compounds of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the mito-met compounds of the present invention is administered to a subject or is used in an assay or other method described herein or a cited reference, e.g., within about 1 hour of the administration or use of the mito-met compounds of the present invention to about 3, 6, 9 months or more after a subject(s) has received the mito-met compounds of the present invention.

By "administering" we mean any means for introducing the mito-met compounds of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection.

By "therapeutically effective amount" we mean an amount effective, at dosages and for periods of time necessary, to achieve the desired therapeutic result, such as reduction or reversal of angiogenesis in the case of cancers, or reduction or inhibition of T-cells in autoimmune diseases. In one embodiment, the therapeutically effective amount ranges from between about 5-50 mg/kg. A therapeutically effective amount of the mito-met compounds of the invention may vary according to factors such as the disease state, age, sex, and weight of the subject, and the ability of the mito-met compounds to elicit a desired response in the subject. Dosage regimens may be adjusted to provide the optimum therapeutic response. A therapeutically effective amount is also one in which any toxic or detrimental effects of the mito-met compounds of the present invention are outweighed by the therapeutically beneficial effects.

A "prophylactically effective amount" refers to an amount effective, at dosages and for periods of time necessary, to achieve the desired prophylactic result, such as preventing or inhibiting the rate of metastasis of a tumor. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

Kits. In another embodiment, the present invention provides a kit comprising a pharmaceutical composition comprising the mito-met compounds of the present invention and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Synthesis of Pyrformin Compounds.

The pyrformin compounds of the present invention are synthesized according to the following reaction:

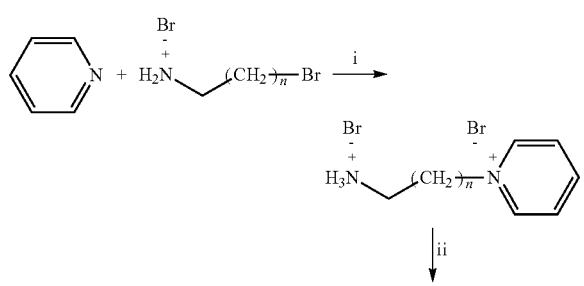

-continued

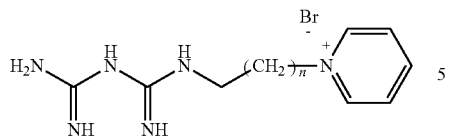

PyrFormin (n = 1)
Pyr$_6$Formin (n = 5)
Reagents and conditions: i, EtOH, reflux; ii, sodium dicyanamide, neat, 180° C.

Example 2

Synthesis of Mito-cy-Metformin Compounds.

The Mito-cy-Metformin compounds of the present invention are synthesized according to the following reaction:

Scheme.

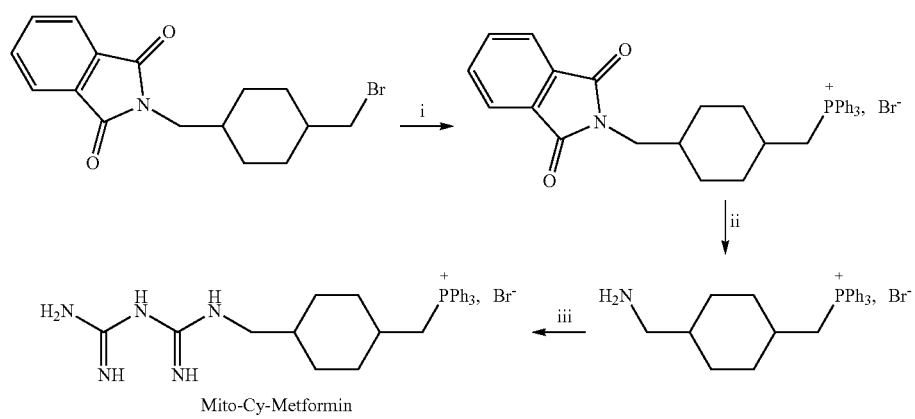

Mito-Cy-Metformin

Reagents and conditions: i PPh$_3$, ACN, reflux; ii; NH$_2$—NH$_2$, EtOH, reflux; iii, HCl, sodium dicyanamide, neat, 180° C.

Example 3

Synthesis of Mito-PEG-Metformin Compounds.

The Mito-PEG-Metformin compounds of the present invention are synthesized according to the following reaction:

Scheme.

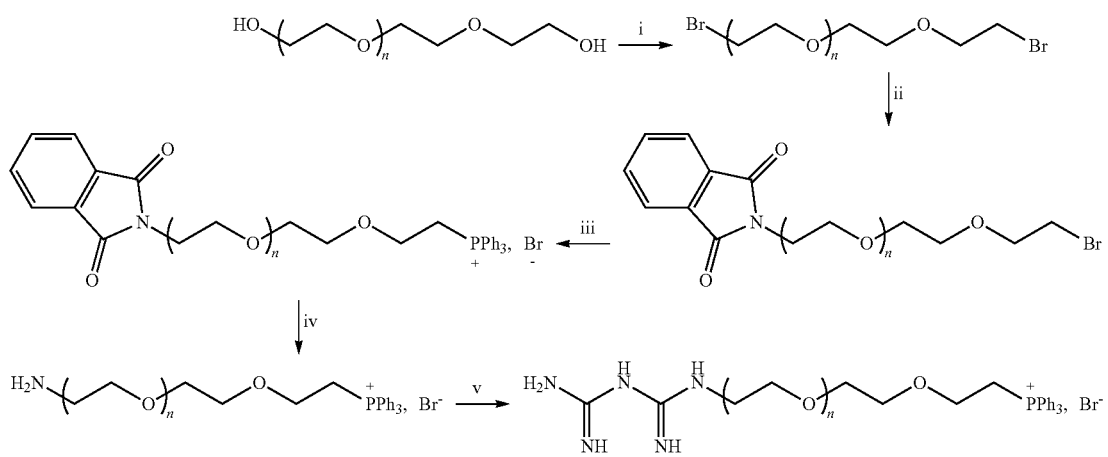

Mito-PEG$_2$-Metformin (n = 1)
Mito-PEG$_3$-Metformin (n = 2)
Reagents and conditions: i, PBr$_3$; ii, Potassium phtalimide, DMF; iii, PPh$_3$, ACN, reflux; iv, NH$_2$—NH$_2$, EtOH, reflux; v, HCl, sodium dicyanamide, neat, 180° C.

Example 4

Synthesis of Mito-Phenformin Compounds.

The Mito-Phenformin compounds of the present invention are synthesized according to the following reaction:

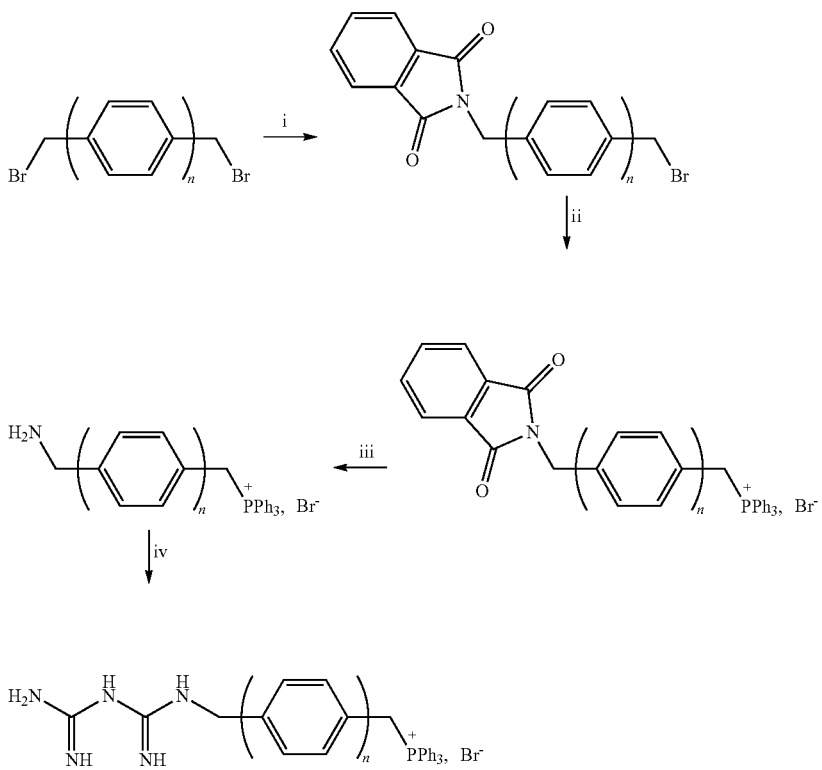

Mito-Phenformin (n = 1)
Mito-Phen₂formin (n = 2)
Reagents and conditions: i, Potassium phtalimide, DMF; ii, PPh₃, ACN, reflux; iii, NH₂—NH₂, EtOH, reflux; iv, HCl, sodium dicyanamide, neat, 180° C.

Example 5

Synthesis of Mito-Metformin Compounds.

The mito-metformin compounds of the present invention are synthesized according to the following reaction:

Scheme.

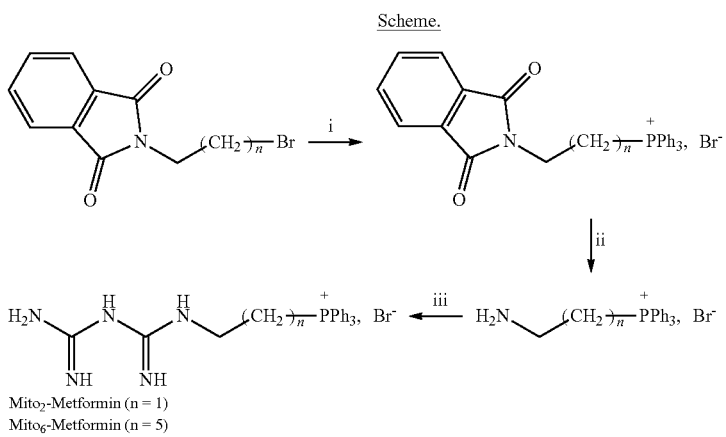

Mito₂-Metformin (n = 1)
Mito₆-Metformin (n = 5)
Mito₁₀-Metformin (n = 10)
Mito₁₂-Metformin (n = 11)
Reagents and conditions: i, PPh₃, ACN, reflux; ii, NH₂—NH₂, EtOH, reflux; iii, HCl, sodium dicyanamide, neat, 180° C.

Example 6

Synthesis of Mito$_2$-Metformin 1

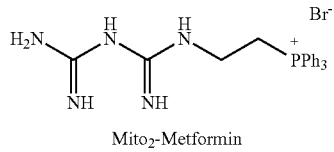

Mito$_2$-Metformin

A 0.1 g portion of (2-Aminoethyl) triphenylphosphonium Bromide (0.26 mmol) was dissolved in CH$_2$Cl$_2$ (3 mL) and the mixture was cooled to 0° C. A 336 µL portion of 1.0 M solution of HCl in diethyl ether (0.33 mmol) was added dropwise. After 1 h 30 at room temperature, the solvent was removed under vacuum. Sodium dicyanamide (0.026 g, 0.31 mmol) was added in BuOH (3 mL). The mixture was heated to reflux overnight, after which the solvent was evaporated and the residue was purified by HPLC to give Mito$_2$-Metformin 1 (0.030 g, 25%).

$^{31}$P NMR, (600.13): δ 21.61. $^1$H NMR, (600.13 MHz): δ 7.93-7.73 (15H, m), 3.80-3.76 (2H, m), 3.38-3.34 (2H, m). $^{13}$C NMR (75.47 MHz) A 158.3 (s), 158.1 (s), 135.1 (s), 133.7 (s), 133.6 (s), 130.3 (s), 131.2 (s), 117.6 (d, J=85), 35.1 (s), 20.6 (d, J=47). HRMS calculated for C$_{22}$H$_{25}$N$_5$P [C$_{22}$H$_{25}$N$_5$P]$^+$ 390.1842, found 390.1842.

Example 7

Synthesis of Mito$_6$-Metformin 4:

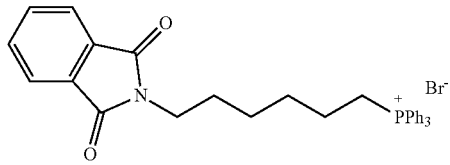

(6-phtalimidyl) triphenylphosphonium Bromide 2. A mixture containing Bromophtalimide (5 g, 0.016 mol) and triphenylphosphane (4.2 g, 0.019 mol) in acetonitrile (60 mL) was refluxed for 15 hours. The solvent distilled under reduced pressure. Purification of the crude product by flash chromatography on a silicagel (CH$_2$Cl$_2$/EtOH 80:20) afforded a white solid 2 (5.7 g, 62%).

$^{31}$P NMR, (400.13): δ 24.38. $^1$H NMR, (400.13 MHz): δ 7.90-7.66 (15H, m), 3.90-3.75 (2H, m), 3.65-3.55 (2H, m), 1.72-1.55 (6H, m), 1.40-1.28 (2H, m). $^{13}$ONMR (75.47 MHz) δ 168.1 (s), 134.84 (s), 134.80 (s), 133.7 (s), 133.4 (s), 133.3 (s), 131.7 (s), 130.4 (s), 130.2 (s), 122.8 (s), 118.5 (s), 118.4 (s), 37.4 (s), 29.2 (d, J=16.5), 26.0 (s), 22.2 (d, J=4.4), 18.2 (s).

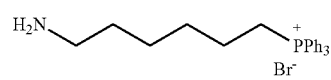

(6-Aminohexyl) triphenylphosphonium Bromide 3. To a solution of 2 (5.2 g, 0.009 mol) in EtOH (70 mL) was added 10 mL of hydrazine 1 M in THF. The mixture was refluxed for 18 hours. The product was purified by flash chromatography on a silicagel (CH$_2$Cl$_2$/EtOH 80:20) afforded a yellow solid 3 (3 g, 75%).

$^{31}$P NMR, (400.13): δ 23.73. $^1$H NMR, (400.13 MHz): δ 7.90-7.66 (15H, m), 3.46-3.39 (2H, m), 2.91 (2H, t, J=7.5), 1.72-1.55 (6H, m), 1.40-1.28 (2H, m). $^{13}$ONMR (75.47 MHz) δ 136.4 (s), 136.3 (s), 134.9 (s), 134.8 (s), 133.0 (s), 131.7 (s), 131.6 (s), 130.9 (s), 127.0 (s), 120.4 (s), 119.6 (s), 40.8 (s), 31.2 (d, J=16.1), 29.0 (s), 26.9 (s), 23.5 (d, J=4.4), 23.0 (s), 22.5 (s).

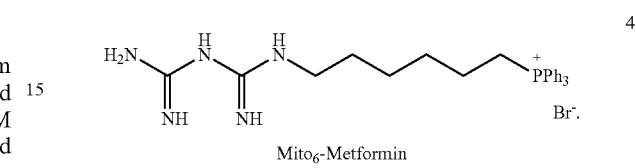

Mito$_6$-Metformin

A 0.1 g portion of (6-Aminohexyl) triphenylphosphonium Bromide (0.23 mmol) was dissolved in CH$_2$Cl$_2$ (3 mL) and the mixture was cooled to 0° C. A 453 µL portion of 1.0 M solution of HCl in diethyl ether (0.45 mmol) was added dropwise. After 1 h 30 at room temperature, the solvent was removed under vacuum. Sodium dicyanamide (0.028 g, 0.33 mmol) was added in BuOH (3 mL). The mixture was heated to reflux overnight, after which the solvent was evaporated and the residue was purified by HPLC to give Mito$_6$-Metformin 4 (0.020 g, 17%).

$^{31}$P NMR, (600.13): δ 24.6. $^1$H NMR, (600.13 MHz): δ 7.93-7.88 (3H, m), 7.81-7.77 (12H, m), 3.60-3.46 (2H, m), 3.05-3.00 (2H, m), 1.55-1.48 (2H, m), 1.48-1.42 (2H, m), 1.41-1.35 (2H, m), 1.31-1.24 (2H, m). $^{13}$C NMR (75.47 MHz) δ 158.2 (s), 157.9 (s), 134.9 (s), 133.6 (s), 133.5 (s), 130.3 (s), 130.2 (s), 118.2 (d, J=86), 40.0 (s), 30.0 (s), 29.5 (s), 25.9 (s), 22.2 (d, J=3), 20.5 (d, J=49). HRMS calculated for C$_{26}$H$_{33}$N$_5$P [C$_{26}$H$_{33}$N$_5$P]$^+$ 446.2468, found 446.2467.

Example 8

Synthesis of Mito$_{10}$-Metformin 7:

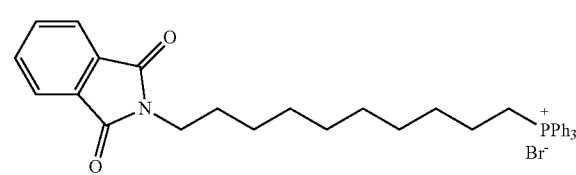

(10-phtalimidyl) triphenylphosphonium Bromide 5. A mixture containing Bromophtalimide (7 g, 0.019 mol) and triphenylphosphane (5 g, 0.019 mol) in acetonitrile (60 mL) was refluxed for 15 hours. The solvent distilled under reduced pressure. Purification of the crude product by flash chromatography on a silicagel (CH$_2$Cl$_2$/EtOH 80:20) afforded a white solid 5 (9 g, 73%). MS calcd for [C$_{36}$H$_{39}$NO$_2$P]$^+$, Br$^-$; [C$_{36}$H$_{39}$NO$_2$P]$^+$, 548.3, found: 548.3.

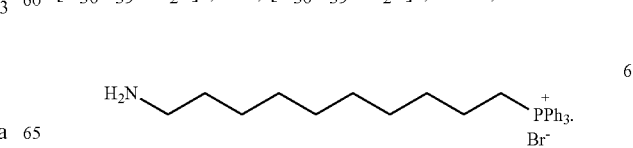

(10-Aminodecyl) triphenylphosphonium Bromide 6. To a solution of 5 (7 g, 0.0108 mol) in EtOH (70 mL) was added hydrazine (0.54 mL, 0.0108 mol). The mixture was refluxed for 15 hours. The solvent is distilled and the impurity was crystallized using a mixture $Et_2O$/EtOH (100 mL+45 mL). The product was purified by flash chromatography on a silicagel ($CH_2Cl_2$/EtOH 80:20) afforded a yellow solid 6 (4 g, 73%). $^{31}P$ NMR (121.49 MHz) δ 24.61. $^1H$ NMR (300.13 MHz) δ 7.95-7.73 (15H, m), 3.70-3.55 (2H, m), 2.80-2.70 (2H, m), 1.60-1.40 (6H, m), 1.35-1.10 (10H, m). MS calcd for $[C_{28}H_{37}NP]^+$, $Br^-$; $[C_{28}H_{37}NP]^+$, 418.2, found: 418.2

7

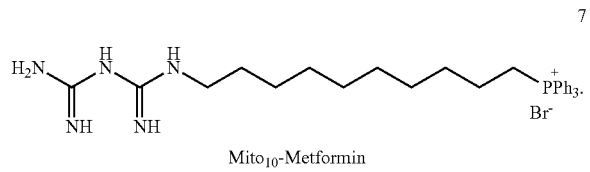

Mito$_{10}$-Metformin

Mito$_{10}$-metformin 7. A 0.2 g portion of (10-Aminodecyl) triphenylphosphonium Bromide 2 (0.4 mmol) was dissolved in $CH_2Cl_2$ (3 mL) and the mixture was cooled to 0° C. a 500 μL portion of 1.0 M solution of HCl in diethyl ether (0.5 mmol) was added dropwise. After 1 h at room temperature, the solvent was removed under vacuum and dicyandiamide (0.034 g, 0.4 mmol) was added in BuOH (2 mL). The mixture was heated to reflux overnight, after which the solvent was evaporated and the residue was purified by HPLC to give Mito$_{10}$-Metformin 3 (0.060 g, 30%). $^{31}P$ NMR, (400.13): δ 23.77. $^1H$ NMR, (400.13 MHz): δ 7.91-7.73 (15H, m), 3.42-3.33 (2H, m), 3.25-3.20 (2H, m), 1.69-1.51 (6H, m), 1.40-1.21 (10H, m). HRMS calculated for $C_{30}H_{41}N_5P$ $[C_{30}H_{41}N_5P]^+$ 502.3094, found 502.3094.

Example 9

Mito-Metformin (Mito-Met) is a Potent Inhibitor of Tumor Formation.

In this example, the inventors show the anti-proliferative potencies of the mito-met compounds of the present invention. Cell proliferation was measured using a label-free, non-invasive cellular confluence assay employing the IncuCyte™ Live-Cell Imaging Analyzer (Essen Bioscience). This system provides real-time cellular confluence data based on segmentation of high definition phase contrast images. MiaPaCa2 (1,000 cells/well) were seeded overnight on a 96-well plate, placed in an XL-3 incubation chamber maintained at 37 C. and cells photographed and confluence calculated every 2 hr by IncuCyte software. MiaPaCa2 cells were treated with Met (1 and 2 mM) or Mito-Met-C10 (1-2 μM). Cell proliferation curves as measured by cell confluence kinetics and representative phase contrast images recorded are shown (FIG. 1).

Figure 7:
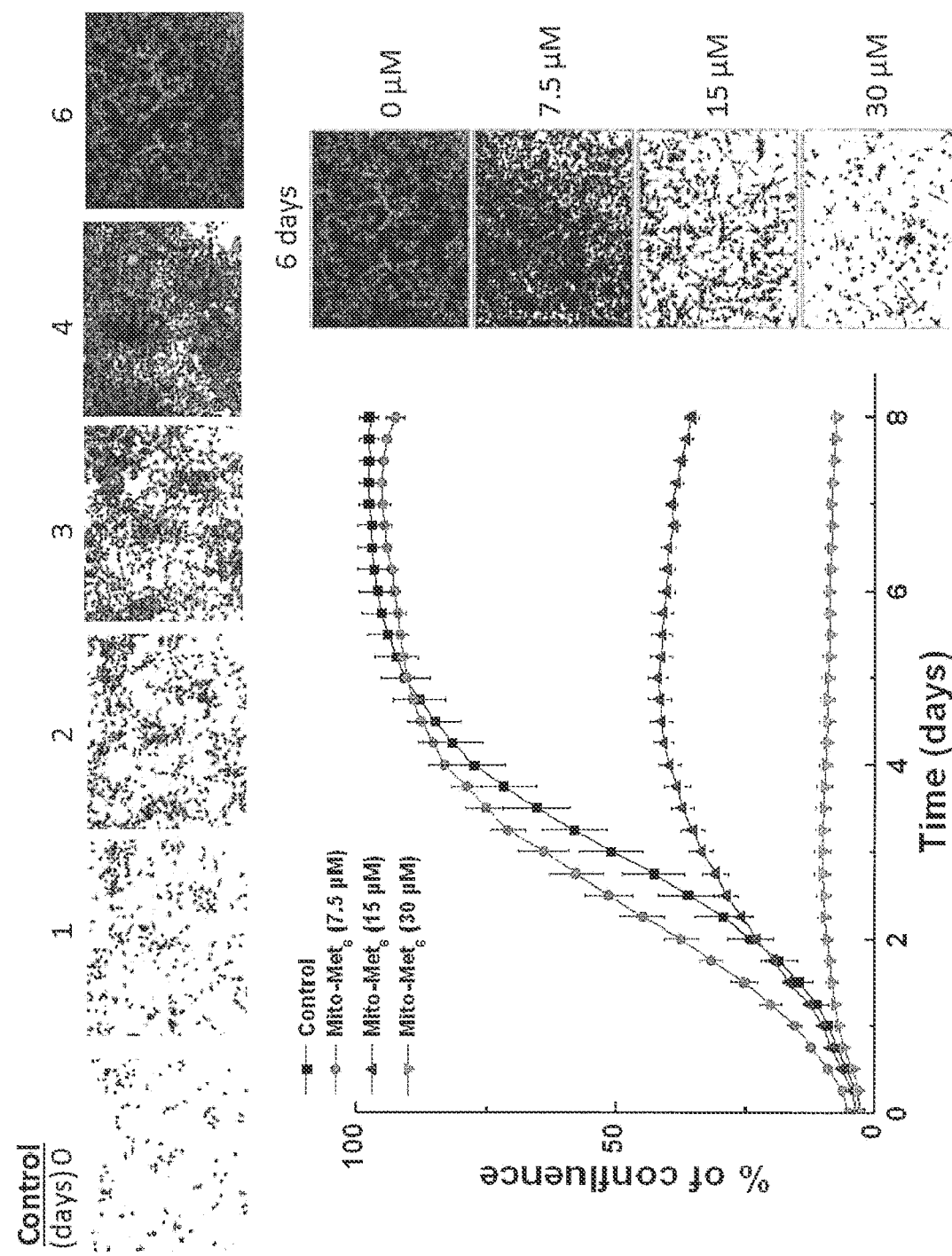
FIG. 7. Effects of mito-meformin-C6 and metformin (control) on PDAC proliferation. MiaPaCa2 cells were treated with mito-metformin-C6 (μM) or metformin (mM) and cell growth monitored continuously until the end of each experiment using the IncuCyte plate reader (Day 0-Day 6). Changes in cell confluence were used as a surrogate marker of cell proliferation. Values are the mean±SD (n=6).
Figure 8:
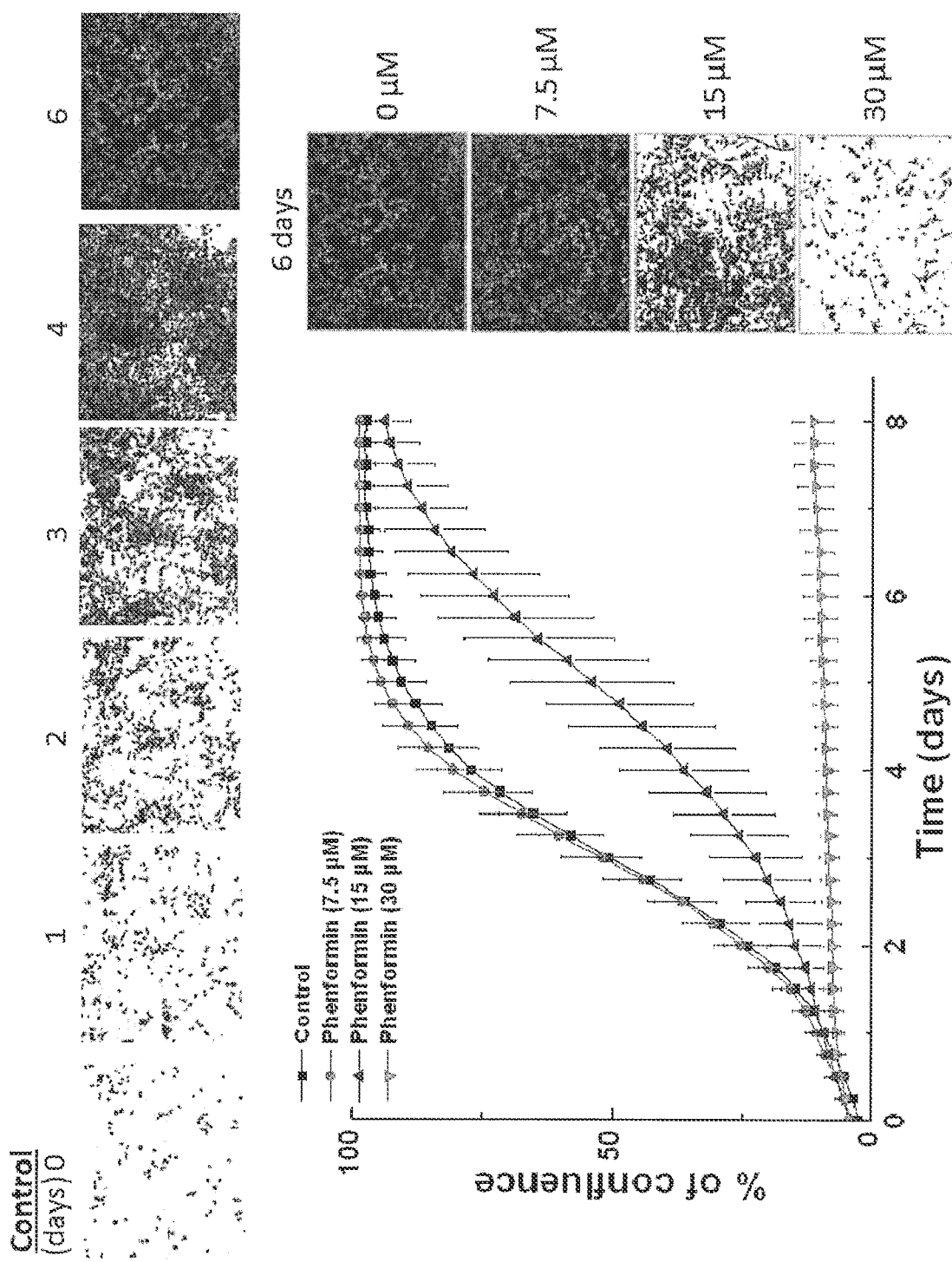
FIG. 8. Effects of phenformin and metformin (control) on PDAC proliferation. MiaPaCa2 cells were treated with phenformin (μM) or metformin (mM) and cell growth monitored continuously until the end of each experiment using the IncuCyte plate reader (Day 0-Day 6). Changes in cell confluence were used as a surrogate marker of cell proliferation. Values are the mean±SD (n=6).
Figure 9:
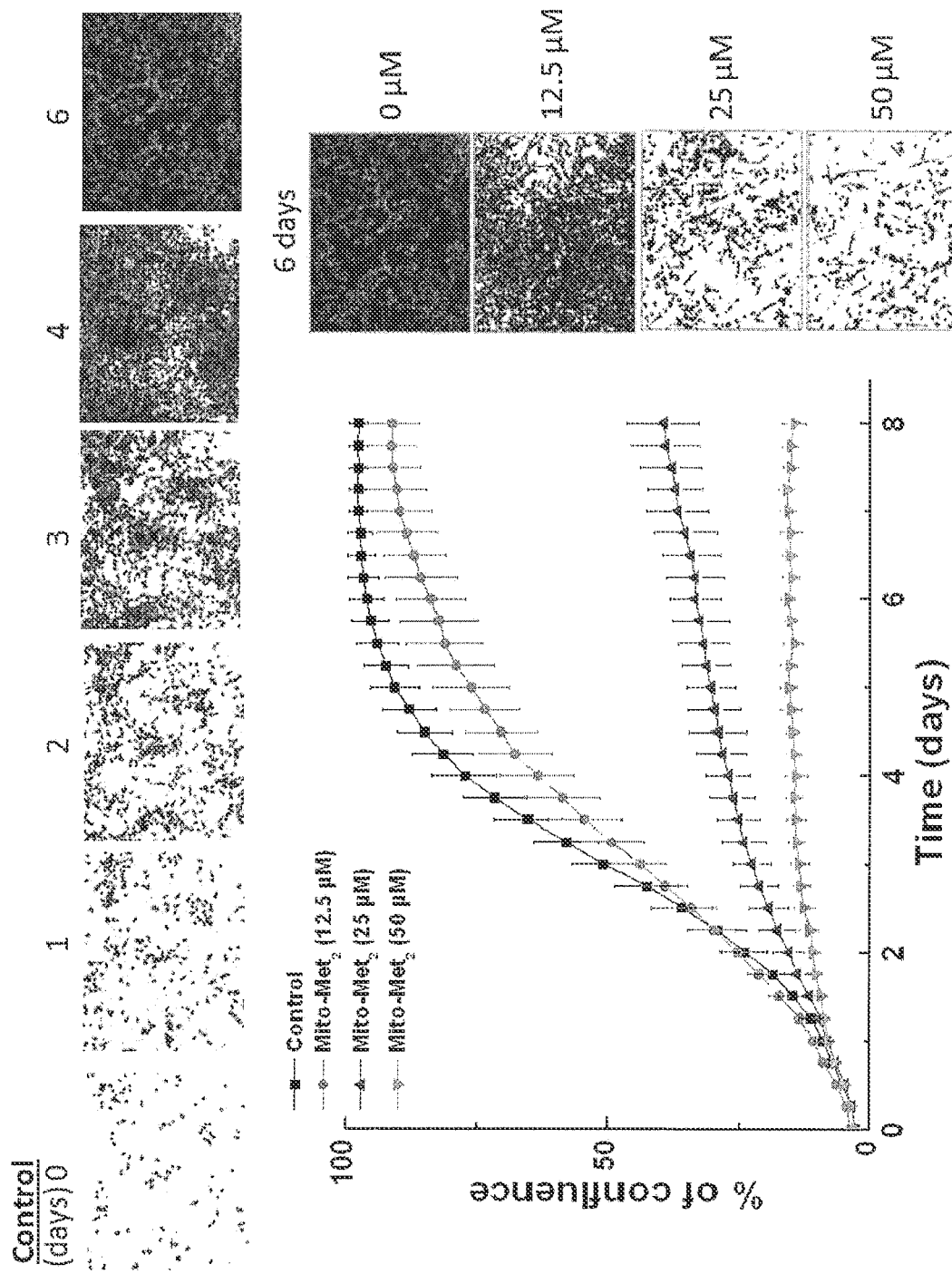
FIG. 9. Effects of mito-metformin-C2 and metformin (control) on PDAC proliferation. MiaPaCa2 cells were treated with mito-metformin-C2 (µM) or metformin (mM) and cell growth monitored continuously until the end of each experiment using the IncuCyte plate reader (Day 0-Day 6). Changes in cell confluence were used as a surrogate marker of cell proliferation. Values are the mean±SD (n=6).

Other mito-met compounds of the present invention were also effective (See FIGS. 6, 7 and 9).

Example 10

Mito-Met Inhibits Tumor Formation.

Figure 3:
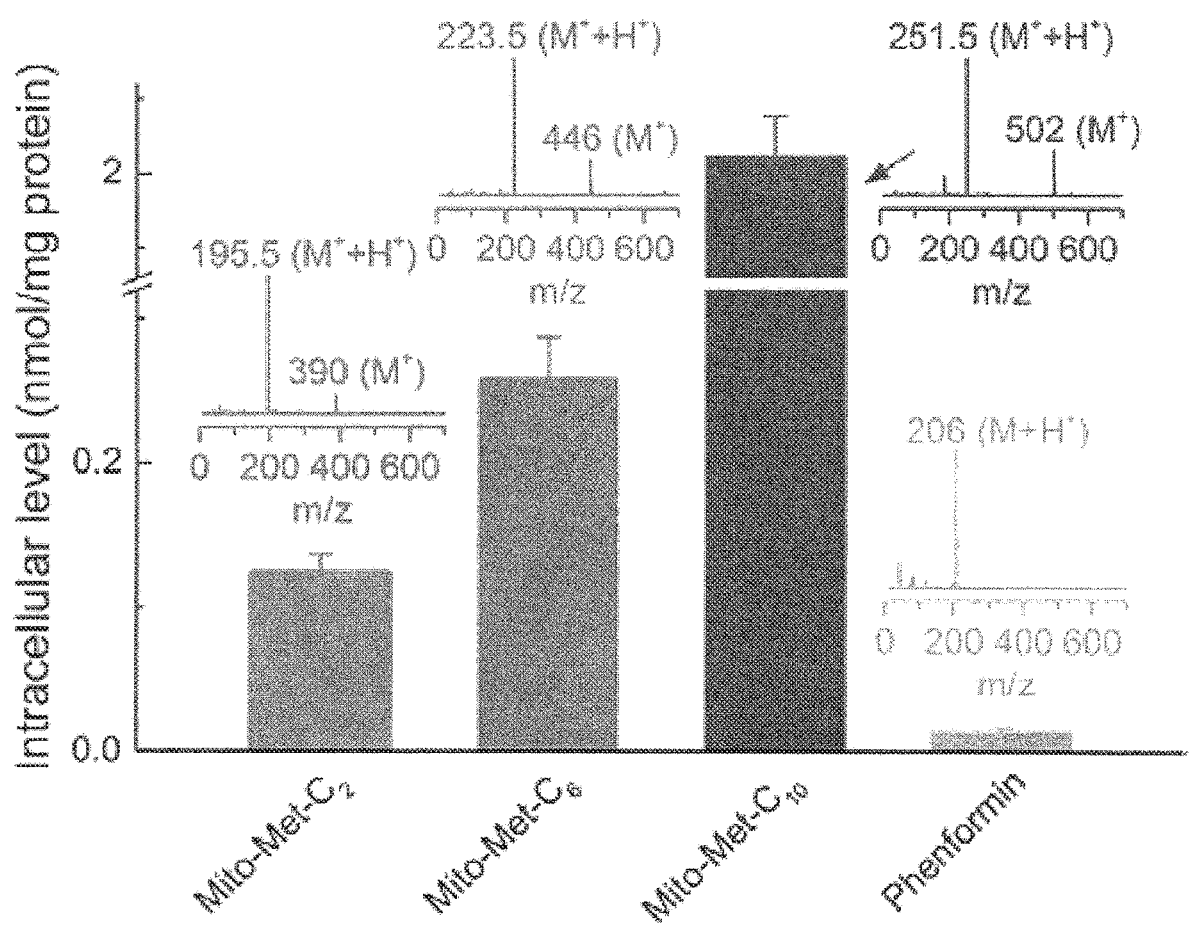
FIG. 3. Cellular uptake of metformin analogs by human pancreatic cancer cells. Cellular uptake of the biguanide phenformin and mito-met analogs with different carbon chain lengths was quantified using LC-MS/MS. Values are mean±SD, n=3.

In this example, the inventors have shown that growth of MiaPaCa2 cells treated with the mito-met compounds of the present invention at a range of concentrations was effectively inhibited (FIGS. 1-3). Preliminary data show that Mito-Met-C10, a synthetic derivative of Met formed by attaching a ten carbon side-chain containing the TPP+ moiety, potently inhibited PDAC proliferation and mitochondrial respiration. The impact of the mito-met compounds of the present invention on energetic metabolism tumor cell proliferation and migration, and in vitro tumor growth and metabolism is shown.

Example 11

Increased Cellular Uptake of the Mito-Met Compounds.

In this example, the inventors show the relative intracellular uptake of various mito-met compounds measured by LC-MS in MiaPaCa2 cells. There is a dramatic increase in Mito-Met cellular uptake as a function of increasing the carbon-carbon side chain. Specifically, Mito-Met-C10 was taken up nearly 100-fold higher than that of phenformin, a Met analog (FIG. 3). Further, results from two independent cell growth assays indicate that the mito-met compounds of the present invention are nearly 1,000-fold more effective than metformin alone in inhibiting PDAC cell proliferation.

Example 12

Increased Potency of the Mito-Met Compounds.

In this example, the inventors show that the mito-met compounds of the present invention are more potent than metformin alone in enhancing PDAC radiosensitivity. MiaPaCa2 cells (1000 cells/well) were cultured in quadruplicate overnight in 96-well plates and changed to fresh medium. Both control cells and cells treated 24 hr with 1 mM metformin were subjected to increasing doses of X-radiation.

As measured using a clonogenic assay (FIG. 2), metformin pre-treatment increased radio-sensitization with decreased MiaPaCa2 cell growth after irradiation.

Example 13

Increased AMPK Activation in Cancer Cells.

In this example, the inventors have shown that the mito-met compounds of the present invention cause an increased AMPK activation in cancer cells. In preliminary experiments (FIG. 4), human MiaPaCa2 and murine FC1199 PDAC cells treated 30 min with 1 μM mito-met (MM), 1 mM Met, or the oligomycin positive control were lysed, and proteins size-separated on SDS-PAGE, transferred to PVDF, and probed with an antibody to phosphorylated AMPK Thr-172. Levels of active protein measured as a ratio of active phosphorylated protein relative to total protein revealed that the mito-met compound evoked a 1.5-2.5-fold increase in active AMPK in BOTH human and murine PDAC cells at 1000-fold lower concentration than metformin alone.

Example 14

Effective Inhibitors.

Metformin (Met), a synthetic analog of the naturally-occurring compound, Galegin, is an FDA-approved anti-diabetic drug that inhibits hepatic gluconeogenesis and exerts anticancer effects in diabetic individuals with pancreatic cancer. Met exists as a hydrophilic cation (FIG. 10A) at physiological pHs and weakly targets mitochondria. A prevailing view is that Met exerts antitumor effects by elevating cellular AMP/ATP ratio and activating the 5-AMP-activated kinase (AMPK)/mTOR pathway and/or by decreasing the circulating insulin levels (and the blood glucose level). Met also inhibits complex I in the mitochondrial electron transport chain, leading to the inhibition of tumor mitochondrial respiration. More recently, metformin was shown to suppress gluroneogenesis by inhibiting mitochondrial glycerophosphate dehydrogenase. The organic cation transporter (OCT) is responsible for Met uptake into tumor cells, while other lipophilic Met analogs (e.g., phenformin) are taken up into cells via other mechanism(s). Phenformin was shown to be considerably more potent than Met in inhibiting pancreatic tumor cell proliferation. An apparent drawback with phenformin is that it was taken off the market in the U.S. because of increased incidence of acidosis reported in antidiabetic therapy. Recent studies, however, recommended additional clinical research repurposing phenformin as a potent antitumor drug.

Previous reports suggest that mitochondria-targeted cationic agents induce antiproliferative and cytotoxic effects in tumor cells without markedly affecting normal cells. For example, conjugating a nitroxide, quinone, a chromanol or Vitamin E to the triphenylphosphonium ($TPP^+$) group via an aliphatic side chain increased their antiproliferative effect in tumor cells. The selective toxicity to tumor cells as compared to normal cells was attributed to enhanced uptake and retention of $TPP^+$-containing compounds in tumor cell mitochondria. Met has been used clinically for over 50 years and has a very good safety profile (diabetic patients tolerate daily doses of 2-3 g). Efforts to improve and enhance efficacy of Met involved modification of structure by attaching alkyl or aromatic groups (e.g., butformin, phenformin) (FIG. 10A).

We now show that improved mitochondria targeting of Met by attaching a positively-charged lipophilic substituent will result in a new class of mitochondria-targeted drugs with significantly increased antitumor potential. To this end, we synthesized and characterized several Met analogs (e.g., Mito-Met$_2$, Mito-Met$_4$, Mito-Met$_{10}$) conjugated to an alkyl substituent containing a $TPP^+$moiety (FIGS. 16A-D), and the present results show that Mito-Met analog (e.g., Mito-Met$_{10}$) (FIG. 10A) is nearly 1,000-fold more effective than Met in inhibiting PDAC proliferation and at least 100 times more effective than Met in abrogating PDAC tumor growth. Reports suggest that Met (1 mM) pretreatment followed by radiation increased radio sensitization leading to enhanced cancer cell killing.

In this example we show that Mito-Met$_{10}$ caused enhancement in radiation sensitivity to the same extent as did Met (1 mM) but at a 1,000-fold lower concentration (1 µM). The significance of the present study is the demonstration that relatively nontoxic mitochondria-targeted metformin analogs alone or in combination with radiotherapy could abrogate pancreas cancer cell proliferation.

Materials and Methods. Cell culture. MiaPaCa-2 and MCF-10A cell lines were obtained from the American Type Culture Collection (Manassas, Va., USA), where they were regularly authenticated. HaCaT and N27 cell lines were stored in liquid nitrogen and used within 6 months after thawing. FC-1242 cell lines were derived from C57BL/6 (B6) KPC transgenic mice that spontaneously developed pancreatic tumors. These cell lines were engineered to express luciferase (KPC-1242-luc) that enabled tumor growth monitoring. Details on cell culturing were previously reported.

Respiratory enzyme activity in intact and permeabilized cells. The mitochondrial function in intact and permeabilized pancreatic cancer cells was measured using a Seahorse XF96 Extracellular Flux Analyzer (Seahorse Bioscience, North Billerica, Mass., USA). Unless specified otherwise, assays in intact cells were performed as previously described. Measurement of mitochondrial respiratory complexes in permeabilized cells was performed according to the manufacturer's instructions (Seahorse Bioscience). Briefly, intact cells were permeabilized using 1 nM Plasma Membrane Permeabilizer (PMP, Seahorse Bioscience) immediately before oxygen consumption rate (OCR) measurement by XF96. The oxygen consumption derived from mitochondrial complex I or complex II activity was measured by providing different substrates to mitochondria, e.g., pyruvate/malate for complex I and succinate for complex II activity. Rotenone, malonate and antimycin A were used as specific inhibitors of mitochondrial complex I, II and III activities, respectively.

Clonogenic assay. The cells were seeded as indicated in six-well plates and treated with Mito-Met$_{10}$ or metformin for 24 h. The plates were kept within the incubator and media changed every 3-4 days until the control cells formed sufficiently large clones. The cell survival fractions were calculated as previously described.

IncuCyte Analyzer-real time measurement of cell proliferation. The cell proliferation was measured using a label-free, noninvasive cellular confluence assay by IncuCyte Live-Cell Imaging Systems (Essen Bioscience, Ann Arbor, Mich., USA; IncuCyte FLR). This system enables collection of live cell images at 2 h intervals over several days. The IncuCyte Analyzer provides real-time cellular confluence data based on segmentation of high-definition phase-contrast images. The cell proliferation is expressed as an increase in percentage of cell confluence.

Three-dimensional spheroid cell cultures of PDAC. MiaPaCa-2 cells (5,000) were seeded in 96-well plates containing Matrigel (Corning), used as scaffold. This typical 3D-cell culture system allows spheroids to form within the matrix. Plates were incubated at 37° C. in a humidified atmosphere with 5% $CO_2$ and the culture media was replaced every two days with treatment at different concentrations (0-1000 µM MitoMet$_{10}$ or 0-10,000 µM metformin). At days 3, 7, and 14 the wells were observed by bright-field microscopy and images acquired on a Nikon Eclipse Ti inverted microscope (Nikon instrument Inc., NY, USA). Spheroid-forming cells were counted using the Nikon NIS Elements imaging software (Nikon). Data are expressed as mean and SD of number of spheroids.

Cytotoxicity assay. To determine the cytotoxicity of Mito-Met analogs and other $TPP^+$-conjugated to a long chain aliphatic hydrocarbon, we used the Sytox assay as described previously. MiaPaCa-2 cells were treated for 24 h, and dead cells were monitored in the presence of 200 nM Sytox Green (Invitrogen). The Sytox method labels the nuclei of dead cells yielding green fluorescence. Fluorescence intensities from the dead cells in 96-well plate were acquired in real time every 15 min after 4 h using a plate reader (BMG Labtech, Inc.) equipped with an atmosphere controller set at 37° C. and 5% $CO_2$:95% air, using a fluorescence detection with 485 nm (excitation) and 535 nm (emission). To measure the total cell number, all of the samples in each treatment group were permeabilized by adding Triton X 100 (0.065%) in the presence of Sytox Green for 3 h, and maximal fluorescence intensities were taken as 100%. Data are represented as a percentage of dead cells after normalization to total cell number for each group.

Immunoblotting. MiaPaCa-2 PDAC cells ($1\times10^6$) were plated to 80% confluency in 60 mm dishes and then serum-starved for 5 hours. Stimulations with metformin or Mito-Met$_{10}$ were performed in serum-free medium. Cells were stimulated with oligomycin as a positive control. After stimulation, cells were washed twice in cold PBS and lysed using a modified RIPA buffer. Lysates were normalized for protein concentration, size separated using reducing SDS-PAGE, electro-transferred to PVDF membranes (Millipore) and then probed using primary and horseradish peroxidase-conjugated secondary antibodies. Antibodies against total or phosphorylated 5' AMP-activated protein kinase (AMPK) were purchased from Cell Signaling Technology (Danvers, Mass.) and used at the manufacturer's recommended dilutions. Proteins were visualized by chemiluminescence with auto-exposure and quantified by densitometric analysis using the FluorChem HD2 from Cell Biosciences (Santa Clara, Calif.).

Quantification of intracellular Mito-Met analogs by LC-MS/MS. Cells were grown on 10 cm dishes and treated with the compounds for 24 h in full media. The protocol for Mito-Met analog extraction from cells was the same as described previously for Mito-Vitamin E using dichloromethane:methanol (2:1) mixture, but without the addition of butylated hydroxytoluene (BHT), a lipophilic chain-breaking antioxidant. LC-MS/MS analyses were performed using Kinetex Phenyl-Hexyl column (50 mm×2.1 mm, 1.7 µm, Phenomenex) equilibrated with water:acetonitrile mixture (4:1) containing 0.1% formic acid. Compounds were eluted by increasing the content of acetonitrile from 20% to 100% over 4 min and detected using the MRM mode.

Radiation experiments. MiaPaCa-2 and MCF-10A cells seeded at $5\times10^5$ in 6-cm dishes were treated with Mito-Met$_{10}$ or metformin for 24 h. The cells were then treated with X-radiation at a dose of 0, 2, 4, and 6 Gy. The control cells were treated with the same concentration of vehicle (0.1% DMSO) where appropriate. After irradiation, cells were suspended and seeded at various densities (100-8,000 cells per well) in 6-well plates for clonogenic assay as described above. The plates were kept within the incubator and media changed every 3-4 days for 2 weeks. Wells with 10-50 sufficiently large clones were chosen for calculating the cell survival fractions.

In vivo studies and bioluminescence imaging. An orthotopic syngeneic engraftment model was used to assess metastatic homing and tumor progression following treatment with metformin or Mito-Metformin-C$_{10}$. Six to eight-week-old C57BL/6 mice were anesthetized with isoflurane and $1\times10^6$ luciferase expressing FC1242 cells. To generate luciferase expressing FC1242 cells, the firefly luciferase gene was cloned into the mammalian expression vector pcDNA3.1/hygro(-) cells transfected using Lipofectamine 2000 transfection reagent (Life Technologies). A cell line stably expressing firefly luciferase was generated by culturing cells in growth medium supplemented with 500 ug/mL hygromycin and limited dilution cloning. A stable clone, named FC1242-luc was expanded to generate a frozen stock. Cells were pretreated for 48 hours with Met (1000 µM) or Mito-Met$_{10}$ (0.5 µM) and then orthotopically engrafted to the pancreas as defined previously for human pancreatic cancer cells. Starting the day of implantation, mice were treated daily with 1 mg/kg Met or Mito-Met$_{10}$ administered via an intraperitoneal injection in a 200 µL volume. Tumor growth and metastasis was monitored using bioluminescence imaging (Lumina IVIS 100, Perkin Elmer, Alameda, Calif.) on days 1, 7, and 13. After 13 days, mice were sacrificed, and primary tumor growth measured using calipers. Metastasis to the liver, mesenteric lymph nodes, spleen and lung was assessed ex vivo using bioluminescence imaging.

Statistical Analysis. All statistical analyses were performed using GraphPad Prism 4 (San Diego, Calif.). Paired analyses were calculated using a student's t-test. Multiple comparisons were analyzed using a one-way ANOVA and a Tukey post-hoc analysis to identify pair-wise differences between distinct experimental groups. Statistical significance was defined as $P \leq 0.05$.

Results-Syntheses and characterization of mitochondria-targeted metformin analogs with varying side chain lengths. The Mito-Metformin analogs were synthesized and characterized by NMR and HR-MS analyses (FIG. 16A-D). Mito-Mets (n=2, 6, 10, and 12) were obtained by reacting the corresponding hydrochloride salt of aminoalkylphosphonium derivative, with dicyanamide neat at 180° C. Mito-Mets were purified by reverse phase preparative-HPLC. Reagents and conditions were: i) PPh$_3$, ACN, reflux; ii) NH$_2$-NH$_2$, EtOH, reflux; iii) 1M HCl in Et$_2$O, dicyandiamide, neat, 180° C. (FIG. 16D).

Mito-Met inhibits PDAC cell and PDAC spheroid growth more potently than Met. Cell proliferation was measured using a label-free, noninvasive cellular confluence assay employing the IncuCyte™ Live-Cell Imaging Analyzer. MiaPaCa-2 cells were treated with Met (100-2,000 µM) or Mito-Met$_{10}$ (0.1-1 µM). Cell proliferation curves, as measured by cell confluence kinetics, and representative phase contrast images recorded (FIG. 10B). Control cells reached 100% confluence in five to six days. Mito-Met$_{10}$ treatment (0.2 and 1 µM) inhibited cell growth by 70% and >90%, respectively (FIG. 10B). In contrast, metformin inhibited cell growth by 80% at 1,000-fold higher concentrations (1,000 µM) (FIG. 10B). A similar trend was noticed at 20% and 1% oxygen (FIG. 10B).

We also monitored colony formation in MiaPaCa-2 cells after a 24 h treatment with Met or Mito-Met$_{10}$ under similar conditions. MiaPaCa-2 cells were treated with a range of concentrations as shown (FIG. 10C), and the number of colonies formed were counted. Almost no colony formation was detected in cells treated with 3 µM of Mito-Met$_{10}$ and 3 mM of Met (FIG. 10C). The survival fraction analysis (FIG. 10D) showed that the IC$_{50}$ values determined for Met and Mito-Met$_{10}$ were 1.3 mM and 1.1 µM, respectively. Thus, results from two independent cell growth assays revealed that Mito-Met$_{10}$ is nearly 1,000-fold more effective than Met in inhibiting MiaPaCa-2 cell proliferation.

Induction of cell death was monitored by Sytox Green staining, as shown previously. MiaPaCa-2 cells were treated with Mito-Met$_{10}$ (100 µM), Mito-CP (100 µM), or Met (30 mM) and other controls for 24 h and cell death was measured in real time. As shown in FIG. 17, there was no detectable cell death even in the presence of 10- to 100-fold higher concentrations (100 µM) of Mito-Met$_{10}$ used in the cell proliferation experiments (FIG. 10B). However, other mitochondria-targeted antiproliferation agents (including, for example and without limitation, Mito-CP, Mito-Q, Mito-CP-Ac, Mito-Tempol, and Mito-chromanol, were considerably more cytotoxic under these conditions (FIG. 17A). Intracellular ATP levels measured under these conditions (FIG. 17B).

We tested the antiproliferative effects of Mito-Met and Met in the multicellular spheroid model (FIG. 11A). MiaPaCa-2 cells were cultured for 14 days in Matrigel and treated with Mito-Met$_{10}$ and Met. As shown in FIG. 11B, Mito-Met (0.5 µM) potently inhibited PPAC spheroid growth, as compared to Met (10,000 µM). Both 2D and 3D cell growth assays indicate that Mito-Met is nearly 1,000- to 10,000-fold more effective than Met in inhibiting PDAC proliferation.

Effects of Mito-Met analogs in normal and cancer cells: Fine tuning alkyl side chain length and potency. We compared the relative antiproliferative potencies of other Mito-Met analogs (Mito-Met$_2$, and Mito-Met$_6$) with Mito-Met$_{10}$, phenformin, and metformin in normal cells and cancer cells. FIG. 12A shows the real-time cellular confluence data of Mito-Met$_{10}$ and metformin in MiaPaCa-2 and nonmalignant control cells, MCF-10A, and HaCaT. In contrast to MiaPaCa-2 or FC1242 pancreatic cancer cells, nonmalignant breast epithelial cells (MCF-10A) or keratinocytes (HaCaT) were not significantly affected in response to Mito-Met$_{10}$ and metformin treatment (FIG. 12A, top and bottom traces). Mito-Met$_{10}$ and Metformin more potently inhibited cellular confluence in MiaPaCa-2 cells as compared to normal cells (HaCaT and N27) (FIG. 12B). FIG. 12C shows the relative potencies of Mito-Met analogs (Mito-Met$_2$, Mito-Met$_6$, and Mito-Met$_{10}$, Phenformin, and Metformin) in inhibiting MiaPaCa-2 cell survival. The IC$_{50}$ value of Mito-Met$_{10}$ was 0.84 µM and that of metformin was 1.1 mM (FIG. 12B). Next we investigated the relative uptake of different Mito-Met analogs (Mito-Met$_2$, Mito-Met$_6$, and Mito-Met$_{10}$) and phenformin in MiaPaCa-2 cells (FIG. 12D). Cells were treated with respective Mito-Met analog (1 µM) for 1 h. Cells were lysed after washing and analyzed for Mito-Met analog by LC-MS. As shown in FIG. 12D, there was a dramatic increase in Mito-Met cellular uptake as a function of increasing carbon-carbon side chain length. As shown in FIG. 12D, Mito-Met$_{10}$ was taken up nearly 100-fold higher than phenformin. Under these treatment conditions, metformin uptake was considerably lower than phenformin.

Effects of Met and Mito-Met analogs on mitochondrial bioenergetics in MiaPaCa-2 cells. The oxygen consumption rate (OCR) and the extracellular acidification rate (ECAR) were measured as a readout of mitochondrial function and glycolysis using a Seahorse Bioscience XF96 extracellular flux analyzer. We compared the immediate OCR changes in response to different concentrations (e.g., IC$_{50}$ or higher values determined by clonogenic assay) of Met, Mito-Met$_2$, Mito-Met$_6$, Mito-Met$_{10}$, and phenformin (FIG. 13A). Metformin dose-dependently decreased the oxygen consumption at relatively higher concentrations ($\approx$1-10 mM). In contrast, the lipophilic phenformin inhibited OCR to the same extent (as did Met) at a ten-fold lower concentration (FIG. 13A). Mito-Met$_{10}$, which inhibited proliferation most potently at sub-micromolar concentration, did not inhibit OCR at 1 µM concentration, although there was a slight inhibition when MiaPaCa-2 cells were treated at a higher concentration of Mito-Met$_{10}$ ($\approx$10 µM). Similar results were observed with Mito-Met$_6$ and Mito-Met$_2$ (FIG. 13A).

Next we monitored the mitochondrial OCR changes in MiaPaCa-2 cells after 24 h treatment with Met, Mito-Met analogs, and phenformin followed by a washout of the treatments and return to fresh cell culture media. In contrast to results shown in FIG. 13A, a significant decrease in OCR was observed in cells after a 24 h treatment with these agents (FIG. 13B). Mito-Met$_{10}$ (1 µM) but not Metformin and methyl-TPP$^+$ most potently inhibited OCR following a 24 h treatment (not shown). Under these conditions (FIG. 13B), ECAR remained mostly unchanged, although there was an initial increase, albeit slight, in ECAR in response to these agents (not shown). These results demonstrate that OCR inhibition was dependent on the chain length and that Mito-Met$_{10}$ inhibited OCR at 1 µM concentration as compared to Mito-Met$_2$ that inhibited at 25 µM (FIG. 13B). The extent of OCR inhibition by Mito-Met analogs increased with increasing length of the alkyl linker (Mito-Met$_{10}$>MitoMet$_6$>Mito-Met$_2$).

Effect of Mito-Met and Met on PDAC radiosensitivity. Both control cells and cells were pretreated for 24 h with 1 mM Met or Mito-Met (1 µM) prior to X-radiation. Cell survival was measured by a clonogenic assay. As shown in FIG. 14A, Met pretreatment increased radiosensitization with decreased MiaPaCa-2 cell growth after irradiation. These results verify the previously reported finding of enhanced PDAC cell killing using Met and radiation. Results show that 1 µM Mito-Met was as effective as 1 mM Met in inducing PDAC radiosensitivity (FIG. 14A), whereas no radiosensitivity was observed in normal cells (MCF-10A) pretreated with Mito-Met$_{10}$ (FIG. 14A). The LC-MS data show a four-fold difference in the intracellular uptake and retention of Mito-Met in MiaPaCa-2 and MCF-10A cells (FIG. 14C).

AMPK activation in Mito-Met and Met-treated PDAC cells. Mitochondria-targeted cationic drugs have been reported to activate bioenergetics stress signaling pathways. We investigated the relative ability of Mito-Met$_{10}$ and Met to activate AMPK-mTOR energy signaling mechanism. Human MiaPaCa-2 and murine FC199 PDAC cells treated with Mito-Met$_{10}$ (1 µM) or Met (1 mM) for 30 min were lysed, proteins size separated on SDS-PAGE were transferred to PVDF, and probed with an antibody to phosphorylated AMPK threonine-172. Levels of active protein measured as a ratio of active phosphorylated protein relative to total protein show that Mito-Met$_{10}$ induces a 1.5-2.5-fold increase in active AMPK in both human and murine PDAC cells at nearly 1,000-fold lower concentration than Met (FIG. 14B).

Figure 20:
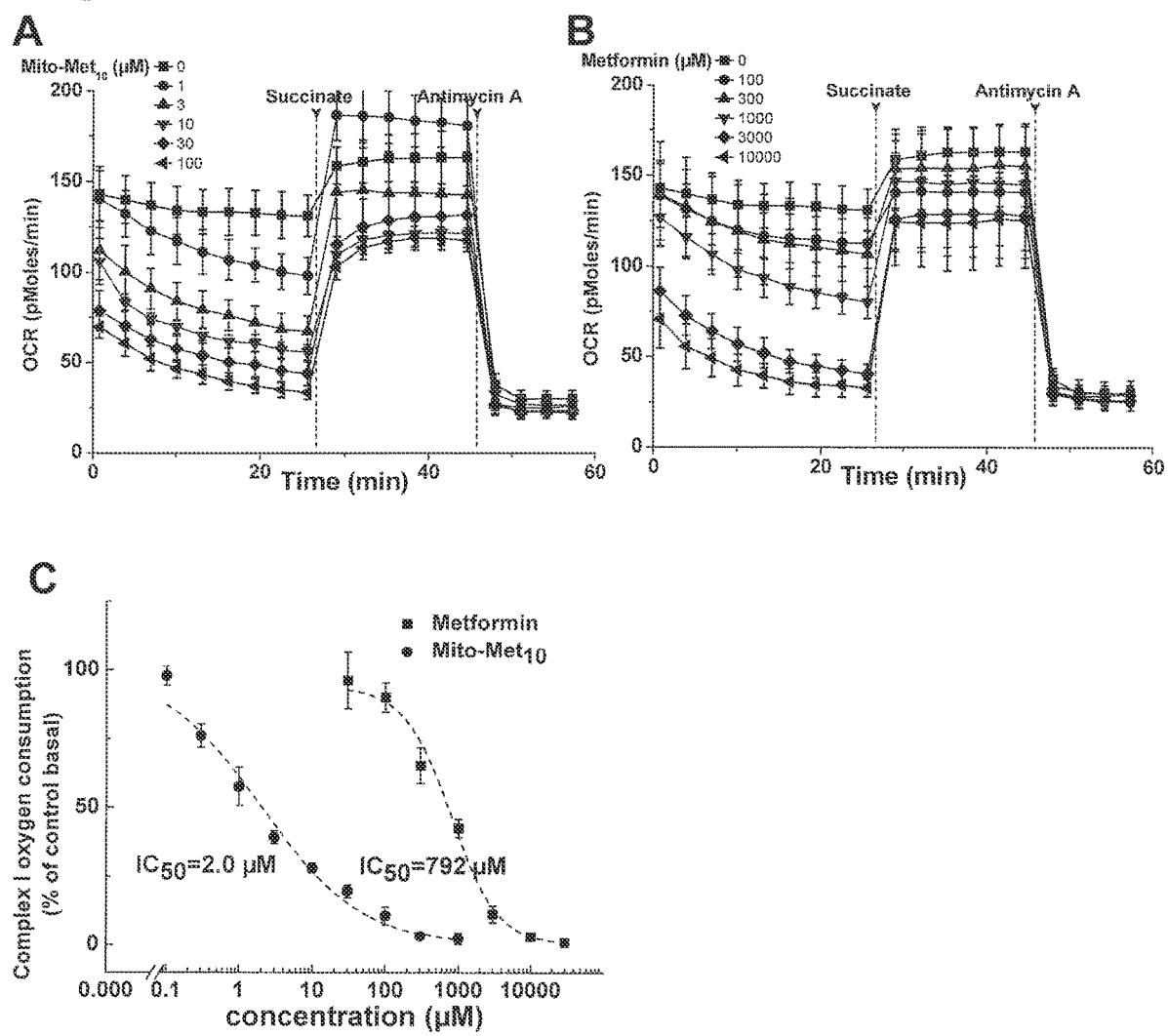
FIG. 20A-C. Mito-Met and Metformin inhibit pyruvate-driven, but not succinate-driven, respiration. Representative experiment of permeablized MiaPaCa-2 cells offered 10 mM pyruvate and 1.5 mM malate in MAS buffer. Either Mito-Met$_{10}$ (A) or metformin (B) were added acutely and OCR was assayed immediately. (C) the mitochondrial complex I oxygen consumption from A and B (last OCR reading before succinate injection) is plotted against concentration. Dash lines represent the fitting curves used for determination of the IC$_{50}$ values. Both succinate (10 mM) and antimycin A (20 µM) were injected where indicated. Data shown are the mean±SD, n=4.
Figure 21:
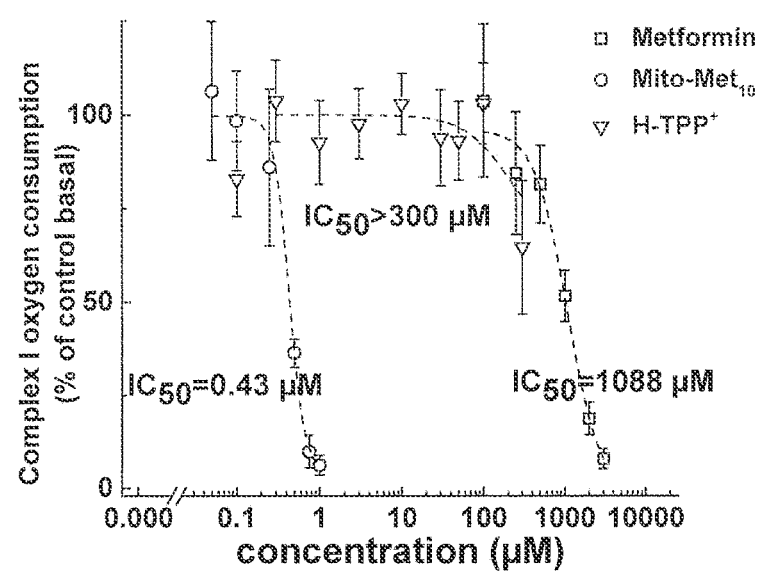
FIG. 21. Mito-Met and Metformin, but not control compound (H-TPP$^+$), inhibit pyruvate-driven respiration. Either Metformin, Mito-Met$_{10}$ or control compound (H-TPP$^+$) were pretreated for 24 h before complex I activity assay (same experimental condition as FIG. 15D). The mitochondrial complex I oxygen consumption (last OCR reading before succinate injection) is plotted against concentration. Dash lines represent the fitting curves used for determination of the IC$_{50}$ values. Data shown are the mean±SD, n=4.
Figure 22:
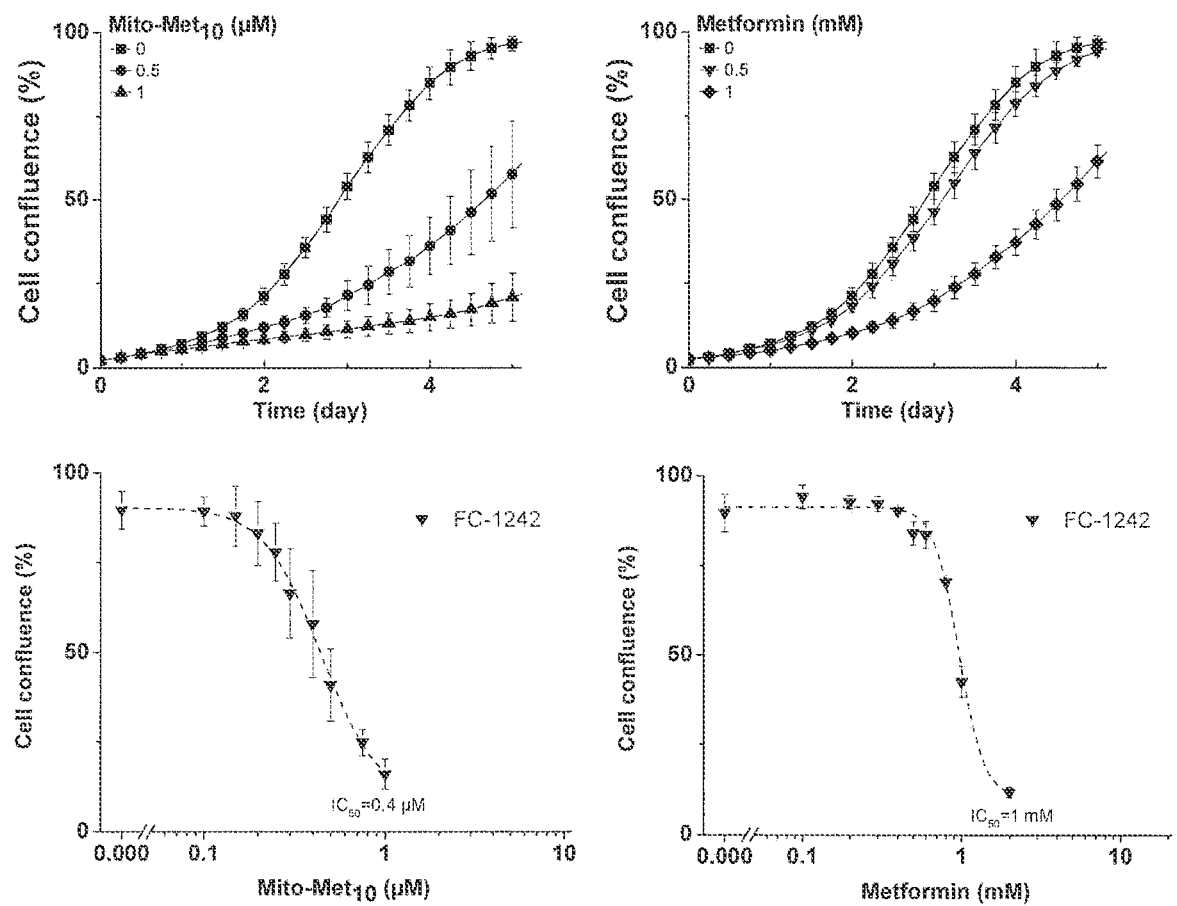
FIG. 22. Effects of metformin and Mito-Met$_{10}$ on mouse pancreatic cancer cell proliferation. Effects of Mito-Met$_{10}$ (left) and Metformin (right) on proliferation under the same conditions as FIG. 10B. Mouse pancreatic cancer cells, FC1242, were treated with Mito-Met$_{10}$ or Metformin and cell growth monitored continuously until the end of each experiment using the IncuCyte. (Bottom) The percentage of cell confluence (as control group reach 90% confluency) is plotted against concentration. Dash lines represent the fitting curves used for determination of the IC$_{50}$ values. Data shown represent the mean±SD, (n=4).

Effects of Mito-Met analogs and Metformin on Complex I activity. The oxygen consumption rate was measured using the permeabilized MiaPaCa-2 cells in MAS buffer supplemented with pyruvate. The use of permeabilized cells avoids differences in cellular uptake of compounds. FIG. 15A shows OCR changes in control permeabilized cells and in rotenone- or malonate-treated cells. Rotenone (complex I inhibitor) greatly diminished OCR that was restored by added succinate. However, in the presence of malonate (complex II inhibitor) addition of succinate did not stimulate OCR (FIG. 15A). Antimycin A decreased succinate-induced OCR. These studies established the use of permeabilized MiaPaCa-2 cells in bioenergetics function assay. Next we used this model to probe the effects of Metformin and Mito-Metformin analogs. Mito-Met$_{10}$ inhibited OCR at much lower concentrations than Met (10 µM versus 3,000 µM) (FIG. 15B and FIG. 20A-C). The IC$_{50}$ values for Met and Mito-Met$_{10}$ were determined to be 792 and 2 µM, respectively (FIG. 20C). We tested the effect of pretreating cells with Mito-Met$_{10}$ or Met using the permeabilized model. MiaPaCa-2 cells were treated with Met and Mito-Met$_{10}$ for 24 h and the oxygen consumption studies were performed in these cells after permeabilization. In contrast to results shown in FIG. 15B, a significant decrease in OCR was observed in permeabilized cells after a 24 treatment with Mito-Met$_{10}$ at a much lower concentration (0.75 µM) for complex I inhibitions (FIGS. 15C-D). The IC$_{50}$ values determined for Met and Mito-Met$_{10}$ in permeabilized cell model were 1.1 mM and 0.4 µM, respectively. This increased potency of Mito-Met$_{10}$ to inhibit complex I activity is consistent with the >1,000-fold enhanced antiproliferative effect of Mito-Met$_{10}$ as compared to Met.

Mito-Met inhibits tumor growth of KPC autografts in vivo. In vivo data show that Mito-Metformin potently halts tumor growth in a preclinical mouse model (FIGS. 15E-G). In an initial proof-of-concept experiment, syngeneic KPC cells expressing Firefly luciferase (FC1242-luc) were orthotopically implanted to the pancreas of C57BL/6 mice and tumor growth monitored using bioluminescence imaging (FIG. 15F). Mice orthotopically autografted with FC1242- luc cells were treated daily with 1 mg/kg or 150 mg/kg Met, or 1 mg/kg Mito-Met. Consistent with the cell culture data, Mito-Met was considerably more effective than Met in abrogating PDAC growth (FIG. 10B) and resulted in markedly smaller primary tumors at the completion of the experiment (FIGS. 6E-F). Serum from these animals was collected, and hepatic and kidney toxicity tested using standard AST, ALT, AP, and BUN assays, respectively. As predicted from cell culture data (FIGS. 10A-D), neither Met nor the mitochondria-targeted analog Mito-Met elicited toxicity in vivo (Table 1).

TABLE 1

| | Toxicity | | |
|---|---|---|---|
| | Liver AST[IU/L] | Liver ALT[IU/L] | Kidney BUN[mg/kg] |
| Control | 85 ± 15 | 17 ± 2 | 22 ± 3 |
| Met [1 mg/kg] | 189 ± 117 | 35 ± 15 | 30 ± 7 |
| Mito-Met[1 mg/kg] | 89 ± 16 | 26 ± 10 | 27 ± 4 |
| Met[150 mg/kg] | 127 ± 24 | 19 ± 3 | 22 ± 2 |

Figure 19:
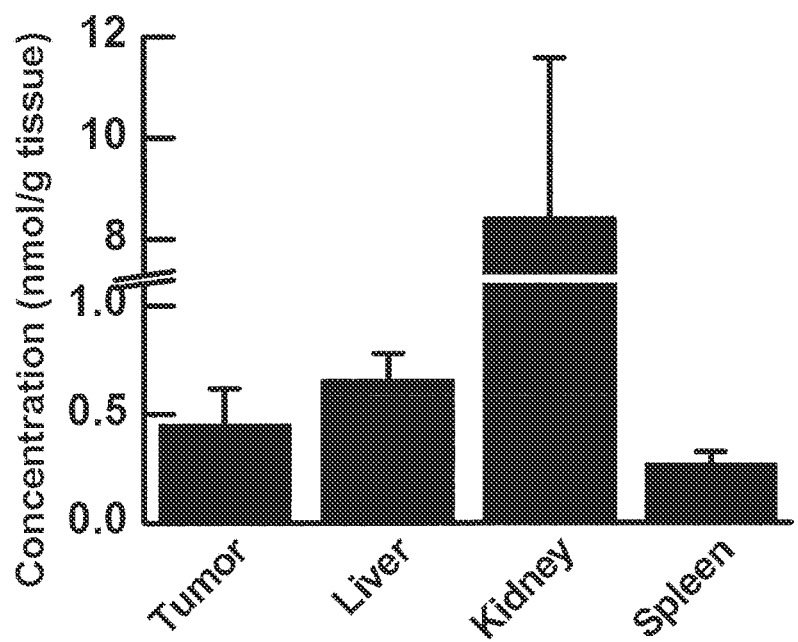
FIG. 19. Tissue accumulation of Mito-Met in in vivo FC1242-luc orthotopic mouse model. FC1242-luc orthotopic mice treated with Mito-Met$_{10}$ (1 mg/kg) daily for 2 weeks. Tissue harvesting and extractions were performed 3 days after the last treatment. Quantitative data on concentrations of Mito-Met after normalization to tissue wet weight are represented as mean±SD, n=5.

Following administration of Mito-Met$_{10}$ for two weeks in FC1242-luc orthotopic mice, we detected an increased accumulation of this compound in liver, kidney, spleen, and tumor (FIG. 19). Collectively, results from these in vivo experiments suggest a therapeutic index of Mito-Met that is nearly 1,000-fold greater than Met, with negligible off-target toxicity.

Discussion. Human pancreatic ductal adenocarcinoma (PDAC) is the most severe and aggressive form of pancreatic cancer with limited chemo- and radiotherapeutic options to improve survival. Currently available standard-of-care chemotherapy offers limited survival benefit. There is critical unmet need for new therapeutic approaches to mitigate therapeutic resistance mechanisms and maximize multimodal treatment approaches in pancreatic cancer. In this study we have developed new mitochondria-targeted metformin analogs that alone and in combination with radiotherapy markedly inhibited PDAC proliferation as compared to metformin. These mitochondria-targeted metformin analogs may have significant clinical and translational potential in PDAC treatment.

Antiproliferative effects of Mito-Metformins in pancreatic cancer cells. Delocalized lipophilic cations (DLCs) inhibit tumor cell proliferation through selective accumulation into mitochondria and inhibition of mitochondrial respiration. Tumor mitochondrial membrane potential has been shown to be much higher (more negative inside) than normal (nontransformed) cells. We previously reported that cationic compounds tethered to an alkyl chain accumulate preferentially in tumor mitochondria depending upon the alkyl side chain length. TPP$^+$-linked agents conjugated to an aromatic and heterocyclic groups (Mito-Chromanol, Mito-CP) also exerted selective cytostatic and cytotoxic effects in various tumor cells. The goal of this study is to modify the hydrophilic cationic metformin into a lipophilic dicationic analog. Metformin exerts biological activity through alterations of cellular bioenergetics without itself undergoing any detectable metabolism. Selective targeting of cancer cell mitochondrial bioenergetics is an emerging chemotherapeutic strategy.

Although several lipophilc variants of metformin were synthesized and shown to exert increased antitumor potency, none of these modifications enhanced mitochondrial targeting cationic function. In this study we showed and characterized, for the first time, that fine-tuning of metformin structure by attaching a TPP$^+$ group tethered to different alkyl chain lengths is synthetically feasible, and that these modified metformins increasingly target tumor mitochondria. Consistent with enhanced intracellular uptake, Mito-Metformin analogs were more potent than metformin in their ability to inhibit pancreatic tumor cell proliferation. The antiproliferative potency of Mito-Met analogs increase with increasing length of the alkyl linker (Mito-Met$_{10}$>Mito-Met$_8$>Mito-Met$_2$) (FIGS. 12C and 18A-B). A major reason for the selective antiproliferative effect of Mito-Met analogs in tumor cells is due to their preferential accumulation in tumor cells as compared to nontransformed (normal) cells.

Proposed mechanism(s) for enhanced antiproliferative and radiosensitizing effects in PDACs. At present, the mechanism(s) responsible for the enhanced antiproliferative and radiosensitizing effects of Mito-Mets in cancer cells remain unknown. It is likely that mitochondria-targeted metformin analogs exert antiproliferative effects in PDACs via targeting the energy sensing bioenergetics pathway(s). Mito-Met$_{10}$ activated AMP-activated protein kinase (AMPK) in MiaPaCa-2 cells nearly 1,000-fold more potently than did metformin (FIGS. 14A-C). AMPK, a master regulator of cellular energy homeostasis, is typically activated by enhanced intracellular AMP. Under conditions wherein intracellular ATP levels are decreased along with a concomitant increase in AMP (enhanced AMP-to-ATP ratio), AMPK is activated via phosphorylation of its threonine-172 residue. Previous research has shown that AMPK represses the Forkhead Box M1 (FOXM1) transcription factor expression through inhibition of the AKT/FOXO3 signaling cascade, leading to regression of cervical cancer cell growth. Thus, it is conceivable that Mito-Met$_{10}$ and related analogs act on the AKT/FOXO3/FOXM1 signaling pathway.

The enhanced radio sensitivity of mitochondria-targeted metformin analogs may be attributed to increased tumor oxygenation (i.e., decreased hypoxia) induced by Mito-Mets. Tumor hypoxia (pO$_2$<10 mmHg), an intrinsic property of numerous solid tumors including the pancreas, results from an imbalance between oxygen delivery and oxygen consumption. Studies suggest that decreasing oxygen consumption with pharmacologic drugs is a more effective route for increasing tumor oxygenation and, in turn, radio sensitivity. Recent reports indicate that metformin (1-10 mM) improves tumor oxygenation and enhances tumor radio sensitivity. The present results show that Mito-Met$_{10}$ decreased mitochondrial respiration in MiaPaCa-2 cells after 24 h (FIG. 13B). Mito-Met$_{10}$ inhibited tumor respiration at micromolar levels, whereas metformin inhibited respiration to a similar extent at millimolar levels. It is likely that Mito-Met$_{10}$ stimulates tumor oxygenation at concentrations 1,000-fold lower than that of metformin. A plausible mechanism by which Mito-Met$_{10}$ decreased mitochondrial respiration is due to enhanced accumulation of Mito-Met$_{10}$ in mitochondria, leading to enhanced inhibition of complex I in the mitochondrial electron transport chain.

In the presence of radiation and Mito-Met$_{10}$ analog, it is possible that two or more mechanisms operate. AMPK-activating drugs enhance tumor radiosensitivity. Radiation itself activates the AMPK energy sensor pathway. However, the degree to which AMPK induces tumor oxygenation and radiosensitivity remains poorly understood.

Recently, it was reported that although metformin inhibits growth of glioblastoma cells and mammalian target of rapamycin (mTOR) pathway, the effects were found to be independent of AMPK. In addition, the same study suggests that AMPK could potentially function as a tumor growth supporter. Metformin-modified mTOR inhibition and suppression of glioma proliferation were attributed to enhanced PRAS40's association with RAPTOR. Clearly, the antiproliferative mechanism of action of Met and Mito-Met may not simply be related to activation of AMPK and other mechanism (i.e., activation of PRAS40/RAPTOR association should also be considered.

Enhanced radio sensitization of PDACS. Metformin versus Mito-Metformin. As reported previously, we found that pre-treatment with Met increased radio sensitization with decreased MiaPaCa-2 cell proliferation (FIGS. 21, 22 & 23A-B). The present data suggest that Mito-Met is significantly more effective than Met in stimulating PDAC radio sensitivity (FIG. 14A-D). Prevailing views suggest that the antiproliferative effects of Met are mediated by activation of the AMPK pathway and/or improved tumor oxygenation (i.e., decreased hypoxia) due to inhibition of mitochondria, leading to decreased tumor cell respiration in irradiated tumors. Tumor hypoxia ($pO_2 < 10$ mmHg) results from an imbalance between oxygen delivery and oxygen consumption. Studies suggest that decreasing oxygen consumption is a more effective route for increasing tumor oxygenation and, in turn, radio sensitivity. AMPK-activating drugs have been shown to enhance tumor radio sensitivity. Mito-Met at concentrations 1,000-fold lower than metformin inhibited mitochondrial respiration and activated AMPK (FIG. 14B).

Clearly, this is an exciting finding with significant potential to clinical translation and requires additional mechanistic studies involving signaling and spectroscopic investigation. More recently, it was shown that at conventional antidiabetic dose of Metformin, there was no significant therapeutic effect in patients with advanced pancreatic cancer. The investigators suggested that more potent biguanides should be used in metabolic treatment of cancer because of vastly reduced plasma concentrations typically detected in diabetic cancer patients treated with Metformin. Mito-Met$_{10}$ exhibiting a 1,000-fold higher potency than Metformin therefore achieves a therapeutically effective plasma concentration in cancer patients.

We claim:

1. A modified metformin compound according to the following structure:

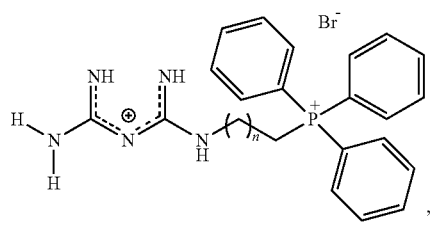

wherein n is an integer selected from 1-11.

2. The mito-metformin compound of claim 1, wherein the mito-metformin is according to the following structure:

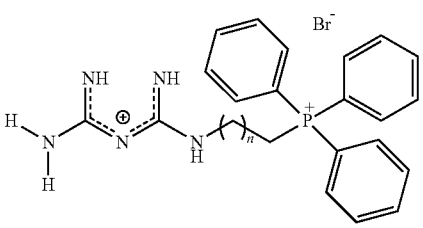

n=1—Mito-Metformin-$C_2$
5—Mito-Metformin-$C_6$
9—Mito-Metformin-$C_{10}$
11—Mito-Metformin-$C_{12}$.

3. The mito-metformin compound of claim 1, wherein the mito-metformin compound is according to the following structure:

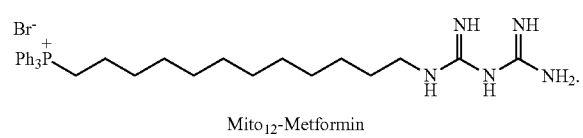

Mito$_{12}$-Metformin

4. The mito-metformin compound of claim 1, wherein the mito-metformin compound is according to the following structure:

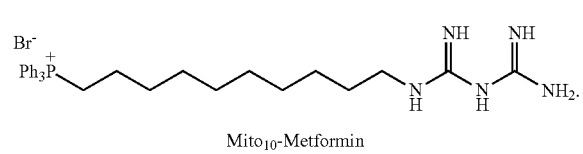

Mito$_{10}$-Metformin

5. The mito-metformin compound of claim 1, wherein the mito-metformin compound is according to the following structure:

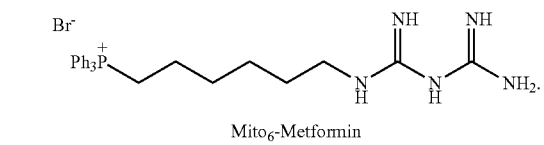

Mito$_6$-Metformin

6. The Mito-Metformin compound of claim 1, wherein the mito-metformin compound is according to the following structure:

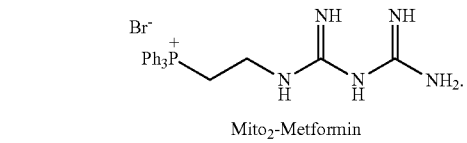

Mito$_2$-Metformin

7. A kit comprising at least one mito-metformin compound of claim 1, a pharmaceutically acceptable carrier or diluent, and instructional material.

8. The kit of claim 7, wherein the kit comprises at least one mito-metformin compound according to the following structure:

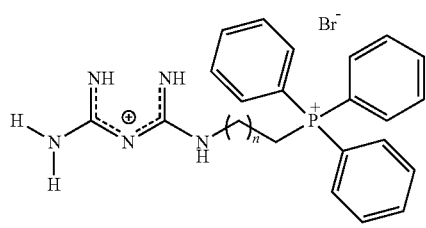

wherein n is an integer selected from 1-11.

9. The kit of claim 7, wherein the mito-metformin compound is selected from the group consisting of mito-metformin compounds according to the following structure:

(a)

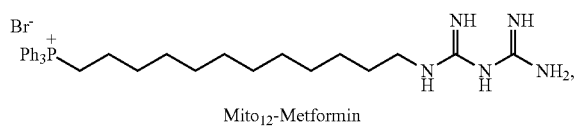

Mito₁₂-Metformin (b)

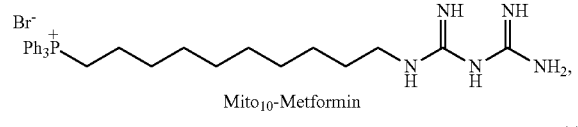

Mito₁₀-Metformin (c)

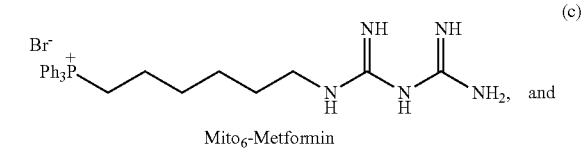

Mito₆-Metformin, and (d)

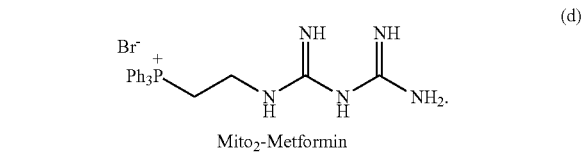

Mito₂-Metformin.

10. A method of inhibiting tumor formation in a subject comprising administering to the subject a therapeutically effective amount of a composition comprising at least one Mito-Metformin compound of claim 1.

11. The method of claim 10, wherein the mito-metformin compound is selected from the group consisting of mito metformin compounds according to the following structure:

(a)

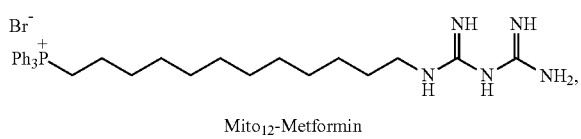

Mito₁₂-Metformin (b)

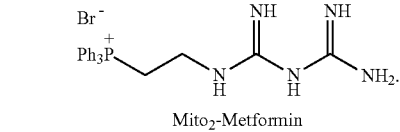

Mito₁₀-Metformin (c)

Mito₆-Metformin, or (d)

Mito₂-Metformin.

* * * * *

UNITED STATES PATENT AND TRADEMARK OFFICE
CERTIFICATE OF CORRECTION

| | |
|---|---|
| PATENT NO. | : 11,274,114 B2 |
| APPLICATION NO. | : 15/503827 |
| DATED | : March 15, 2022 |
| INVENTOR(S) | : Balaraman Kalyanaraman et al. |

It is certified that error appears in the above-identified patent and that said Letters Patent is hereby corrected as shown below:

On the Title Page

Item (12) should read:
Kalyanaraman, et al.

Item (72) Inventors:
"Balaraman Kalyanaramn" should be --Balaraman Kalyanaraman--.

Signed and Sealed this
Nineteenth Day of September, 2023

Katherine Kelly Vidal
*Director of the United States Patent and Trademark Office*